(12) United States Patent
Kato

(10) Patent No.: US 10,345,100 B1
(45) Date of Patent: Jul. 9, 2019

(54) APPARATUS AND METHOD FOR EVALUATING METAL SURFACE TEXTURE

(71) Applicant: PaPaLaB Co., Ltd., Hamamatsu-shi, Shizuoka (JP)

(72) Inventor: Makoto Kato, Hamamatsu (JP)

(73) Assignee: PaPaLaB Co., Ltd., Hamamatsu-shi (JP)

( * ) Notice: Subject to any disclaimer, the term of this patent is extended or adjusted under 35 U.S.C. 154(b) by 63 days.

(21) Appl. No.: 15/854,829

(22) Filed: Dec. 27, 2017

(51) Int. Cl.
| | |
|---|---|
| *G01B 11/30* | (2006.01) |
| *G06K 9/62* | (2006.01) |
| *G06K 9/46* | (2006.01) |
| *G01J 3/46* | (2006.01) |
| *G01J 3/02* | (2006.01) |
| *G01J 3/51* | (2006.01) |
| *G01J 3/52* | (2006.01) |

(52) U.S. Cl.
CPC ............ *G01B 11/30* (2013.01); *G01J 3/0208* (2013.01); *G01J 3/462* (2013.01); *G01J 3/465* (2013.01); *G01J 3/51* (2013.01); *G01J 3/52* (2013.01); *G06K 9/4642* (2013.01); *G06K 9/4652* (2013.01); *G06K 9/6201* (2013.01); *G06K 9/6212* (2013.01)

(58) Field of Classification Search
CPC . G01B 11/30; G01J 2003/2813; G01J 3/0202; G01J 3/10; G01J 3/462; G01J 3/465; G01J 3/50; G01J 3/504; G01J 3/51; G06K 9/4642; G06K 9/4652; G06K 9/6201; G06K 9/6212
See application file for complete search history.

(56) References Cited

U.S. PATENT DOCUMENTS

2016/0140734 A1* 5/2016 Kato .................... G06K 9/4642
348/222.1

FOREIGN PATENT DOCUMENTS

| JP | 7-280541 A | 10/1995 |
|---|---|---|
| JP | 8-43060 A | 2/1996 |
| JP | 10-227626 A | 8/1998 |
| JP | 2005-257827 A | 9/2005 |
| JP | 2014-187558 A | 10/2014 |

\* cited by examiner

*Primary Examiner* — Hina F Ayub
*Assistant Examiner* — Amanda Merlino
(74) *Attorney, Agent, or Firm* — Matthias Scholl, PC; Matthias Scholl

(57) ABSTRACT

An object is to quantify the texture such as irregularity and gloss of a metal surface. Centers of Lab chromaticity distributions are identified (S145), and one of the Lab chromaticity distribution is entirely shifted (mapped) by deviations $\Delta A$, $\Delta B$ and $\Delta L$ of a central coordinate, such that one of central coordinates of two distributions $U_1(L,a,b)$ and $U_2(L,a,b)$ matches with the other central coordinate (S146). A texture spread index that indicates a difference in spatial spread is then computed (S147). This configuration computes the spatial spread of the Lab chromaticity distribution in a three-dimensional space, and quantifies the irregularity of an inspection plane by diffraction phenomenon of illumination light. The difference in spread other than the color is applicable to evaluation of the irregularity of the metal surface or the like.

2 Claims, 19 Drawing Sheets

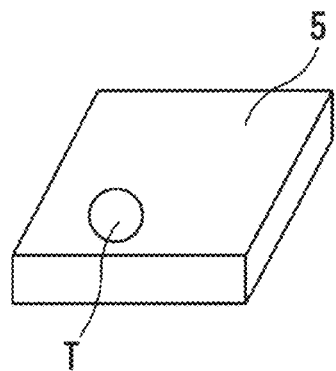
FIG. 8A
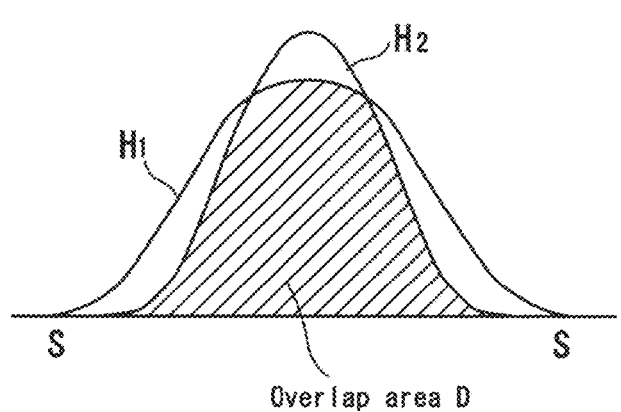
FIG. 8D
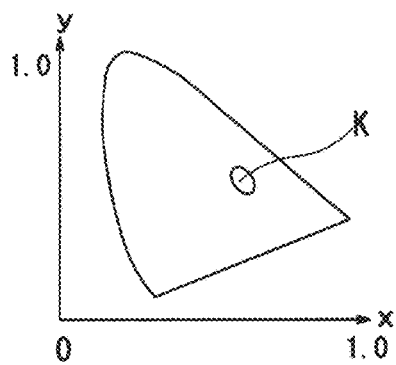
FIG. 8B
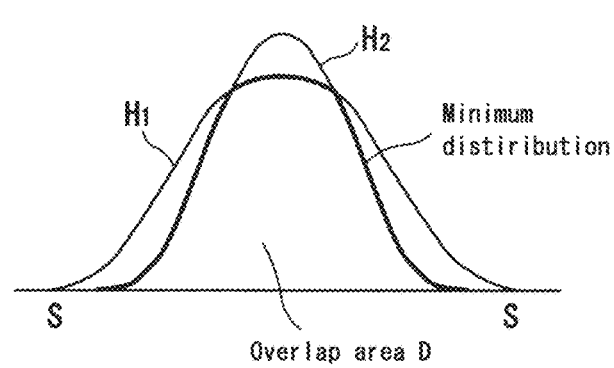
FIG. 8E
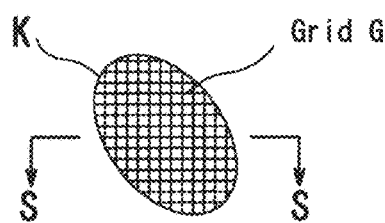
FIG. 8C
FIG. 8F Imaging measurement objects 1 to 3

Integrating color information in measurement range

Distribution diagram on xy chromaticity diagram of color 1 to 3

Three-dimensional diagram of integrated data of color
( Z axis corresponds to counting value )

Measurement range and measurement area of sample (within square frame in image)

Reference brown turbidity non-brown turbidity

Measurement range and measurement area of sample
(within square frame in image)

Reference brown turbidity non-
brown turbidity

APPARATUS AND METHOD FOR EVALUATING METAL SURFACE TEXTURE

CROSS-REFERENCE TO RELATED APPLICATIONS

The contents of Japanese Appl. No. 2016-131126 filed Jun. 30, 2016 are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

TECHNICAL FIELD

The present disclosure relates to a texture evaluation apparatus and a texture evaluation method of metal surface and more specifically relates to an evaluation apparatus configured to evaluate texture, such as gloss, unevenness, cloudiness, irregularity and the like, of metal surface as well as an evaluation method.

BACKGROUND

Various methods have been proposed to polish the fine irregularity on a metal surface (http://www.chemicoat.co.jp/column/detail_6.html).

"Chemical polishing" denotes a polishing technique that soaks a metal in a solution for polishing, in order to corrode the surface of the metal by chemical reaction of an acid or an alkali. The solution enters even a small part to process the small part, which is not processible by mechanical polishing. Chemical polishing is mainly suitable to polish a microcomponent of a complicated shape or an internal surface.

"Electrolytic polishing" denotes a polishing technique that soaks a metal in a solution for electrolytic polishing and polishes the metal as the positive electrode in the solution by the flow of electric current. The metal is gradually electrolyzed to give a gloss or a smooth surface. This technique does not make any altered layer on the surface by processing and does not leave any stain or burn. Electrolytic polishing as well as chemical polishing is used for, for example, precision components that require a clean polishing technique.

"Mechanical Polishing" denotes a polishing technique using a machine and includes various methods. A rotary polishing technique is a currently dominant technique that applies a polishing pad on a disk-shaped surface plate, drops down a liquid polishing agent including a chemical component and fine particles on the polishing pad, and polishes the surface with the rotating polishing pad. Other polishing techniques include a method of precisely polishing an inner diameter of a metal with a honing machine and buffing using a buff.

Satin finish (http://www.chemicoat.co.jp/knowledge/detail_169.htmol) is a surface treatment method that forms fine concaves and convexes on the surface of a metal to provide rough texture. Satin finish is also called pear-skin finish, since the finished surface is similar to the surface of a fruit, pear. Satin finish includes gloss finish, semi-gloss finish and matte finish. Satin finish is employed for the purpose of improving the texture and the appearance, for the purpose of anti-slip to help the grasp of an oily hand, and for the purpose of pretreatment of coating or anodization. "Manual scraping" may be employed to form fine concaves and convexes, in order to reduce the friction resistance of the metal surface of, for example, a precision machine.

Satin finish of the metal surface mainly includes mechanical methods and chemical methods. The mechanical methods include a wire brushing method that polishes the metal surface with a wire brush, a sand blast method that sprays fine particles against the surface by the compressed air, and a liquid honing method that sprays a processing solution including fine particles onto a target surface of metal processing, in addition to the manual scraping described above. The chemical methods of satin finish include a method of chemical corrosion or galvanic corrosion such as etching and a surface treatment method using electroplating such as dispersal plating.

Roughness meters are generally used for measurement of the surface gloss or roughness. The roughness meters include mechanical types and optical types using, for example, laser. The roughness meter provides a numerical indication of the irregularity in the unit of millimeter or in the unit of nanometer. A skilled worker in the field evaluates the surface condition by visually checking the gloss and the shine of the surface, rather than the numerical measurement. The work generally proceeds, based on the result of evaluation by the skilled worker in the field.

CITATION LIST

Patent Literature

Patent Literature 1: JP H07-280541A
Patent Literature 2: JP H08-43060A
Patent Literature 3: JP H10-227626A
Patent Literature 4: JP 2014-187558A The techniques disclosed in Patent Literatures 1, 2 and 3 have been proposed for optical measurement of the surface.

The technique disclosed in Patent Literature 4 has been proposed for adjustment of the color and the space. This proposed technique uses a camera configured to have three spectral sensitivities ($S1(\lambda)$, $S2(\lambda)$, $S3(\lambda)$) linearly and equivalently converted to a CIE XYZ color matching function; an arithmetic processor configured to obtain and compute coloring data by conversion of an image that has three spectral sensitivities and that is obtained by the camera, into tristimulus values X, Y and Z in a CIE XYZ color system; and a lighting unit configured to illuminate a measurement object. The arithmetic processor is configured to: set a specified inspection area in the coloring data obtained by imaging the measurement object; compute x and y values of the inspection area normalized from X, Y and Z values of each pixel in the inspection area with regard to an inspection object and a reference object as the measurement objects; divide the inspection area into grids in xy coordinates of an xy chromaticity diagram and integrate number of pixels included in each grid with respect to the inspection object and the reference object, so as to create respective xy chromaticity coordinate histogram distributions or integrate number of pixels in an XYZ chromaticity coordinate histogram obtained in three-dimensional XYZ coordinates, so as to create an XYZ chromaticity coordinate histogram distribution; and compute Lab average values and a spread difference indicating an overlap degree of the two xy chromaticity coordinate histogram distributions or the two XYZ chromaticity coordinate histogram distributions of the inspection object and the reference object, so as to inspect color and texture.

This technique totally inspects the color and the texture and is accordingly correlated to the human visual recognition. This technique is employed, for example, in an in-line camera device for industrial products. In the flow of industrial products, this technique is used to detect, in real time, a color difference of the entire industrial product or a color difference on the boundary between parts of the industrial product like the human visual recognition. This technique accordingly excludes coloring failures based on the criterion similar to that of the human visual recognition.

SUMMARY OF INVENTION

Technical Problem

The techniques disclosed in Patent Literatures 1 to 3, however, fail to evaluate the texture indicating the finishing quality, such as gloss, glaze, roughness and the like. The technique disclosed in Patent Literature 4 uses a color consistency index as a parameter for totally adjusting the color and the texture. This is convenient for in-line color inspection but may not be suitably used for evaluation of the texture indicating the finishing quality of the metal surface.

Finishing the metal surface may be, for example, rough finishing or mirror finishing. The expert's visual evaluation is required to determine the degree of roughness. The rough finishing of the metal surface has irregularity in the micrometer order, and the mirror finishing of the metal surface has irregularity in the nanometer order. The human visual evaluation in the micrometer order and in the nanometer order takes both the time and the cost and moreover has difficulty in accurate determination.

An object of the present disclosure is to quantify the finishing quality of a metal surface under conditions close to conditions of human visual evaluation by measuring a reflected light distribution of irregularity of the metal surface that is irradiated with light from a light source, with an XYZ system camera and observing the light from the light source as a spread of color by diffraction according to the configuration of the metal surface.

Solution to Problem

The present disclosure provides evaluation using an XYZ system camera and allows for evaluation that is significantly close to the human visual recognition. This is because the camera two-dimensionally or three-dimensionally provides accurate values. The texture such as irregularity of the inspection plane may be quantified by the diffraction phenomenon of illumination light.

By taking into account the above problem, the present disclosure is based on the findings that in measurement of a reflected light distribution of a metal surface illuminated with a light source using an XYZ system camera of the present disclosure, the light from the light source is observed by diffraction as a spread of color and texture according to the configuration of the metal surface, and the color and texture such as gloss, glaze, unevenness, cloudiness, irregularity and the like of the metal surface are quantified by this spread. According to one aspect of the present disclosure, there is provided a texture evaluation apparatus of a metal surface, including: a camera configured to have three spectral sensitivities (S1(λ), S2(λ), S3(λ)) linearly and equivalently converted to a CIE XYZ color matching function; an arithmetic processor configured to obtain and compute data by conversion of an image that has three spectral sensitivities and that is obtained by the camera into tristimulus values X, Y and Z in a CIE XYZ color system; and a light source configured to illuminate a metal surface, wherein the arithmetic processor is configured to: set a specified inspection area out of data obtained by imaging the metal surface; divide the inspection area into grids in coordinates corresponding to a color space in an XYZ color system, and integrate number of pixels included in each grid with respect to an inspection plane and a reference plane, so as to create respective color space histogram distributions in the XYZ color system; and identify centers of the two color space histogram distributions of the inspection plane and the reference plane, and compute a texture spread index indicating a difference in spread between the color space histogram distributions by shifting the center of one of the color space histogram distributions to be closer to the other color space histogram distribution.

The metal surface herein may be, for example, surface of a cutting tool, surface of a mold or surface of plating. The texture includes, for example, gloss, glaze, roughness and irregularity. The evaluation means that the finishing quality such as the irregularity, unevenness, cloudiness, roughness, glaze and gloss of the metal surface is evaluated.

According to another aspect, there is provided a texture evaluation method of a metal surface using a camera configured to have three spectral sensitivities (S1(λ), S2(λ), S3(λ)) linearly and equivalently converted to a CIE XYZ color matching function, the texture evaluation method including: generating data by conversion of an image that has three spectral sensitivities and that is obtained by imaging with the camera under lighting into tristimulus values X, Y and Z in a CIE XYZ color system; setting a specified inspection area out of data obtained by imaging a metal surface; dividing the inspection area into grids in coordinates corresponding to a color space in an XYZ color system, and integrating number of pixels included in each grid with respect to an inspection plane and a reference plane, so as to create respective color space histogram distributions in the XYZ color system; and identifying centers of the two color space histogram distributions of the inspection plane and the reference plane, and computing a texture spread index indicating a difference in spread between the color space histogram distributions by shifting the center of one of the color space histogram distributions to be closer to the other color space histogram distribution.

The term "XYZ color system" is used in a broad sense including other CIE color systems in the claims, while being used in a narrow sense in the description other than claims. The XYZ color system in the narrow sense is determined to cause an RGB color space not to take any negative value by simple linear transformation. The XYZ color system in the narrow sense is used as the basis of other CIE color systems, for example, Yxy, XYZ, Lab and Luv and is a concept including a two-dimensional chromaticity diagram or a three-dimensional color space. Accordingly, the XYZ color system in the broad sense includes the XYZ color space in the narrow sense and other CIE color spaces developed from the XYZ color system in the narrow sense.

The XYZ color system in the narrow sense is a color space determined in 1931 by CIE to cause the RGB color space not to take any negative value by simple linear transformation, simultaneously with the RGB color system.

The xyY color system (also called Yxy color system) is determined to express the absolute color from the XYZ color system, since the relationship between the numerical value and the color is not readily understandable in the XYZ color system.

The Luv color system is one of uniform color spaces determined in 1976 by CIE. The CIE L*u*v* color space improves the uniformity of the wavelength interval in the xy chromaticity diagram of the XYZ color system, on the basis of the wavelength of light and is specified by JIS Z8518 in Japan.

The Lab color system denotes a CIE L*a*b* color space and is derived from the XYZ color system to measure a color difference due to the difference between perception and the instrumental measurement and is specified by JIS Z8729 in Japan.

The XYZ color space in the broad sense includes color spaces specified by two-dimensional coordinates and color spaces specified by three-dimensional coordinates. Typical examples of the color space include an XYZ color space and a Lab color space. In the case of the two-dimensional color space, for example, Yxy color space or Luv color space, an xy chromaticity diagram (xy chromaticity value (plane) normalized in the Yxy color space), a uv chromaticity diagram, and a u'v' chromaticity diagram are examples of the two-dimensional plane. This corresponds to, for example, an xy chromaticity histogram distribution or an Luv chromaticity histogram distribution expressed as the density of pixels of the two-dimensional chromaticity diagram on the plane. In the case of the three-dimensional color space, for example, the XYZ color space of the Lab color space, an XYZ color space and a Lab color space are examples of the three-dimensional space. This corresponds to, for example, an XYZ color space histogram distribution or a Lab color space histogram distribution expressed as the density of pixels on the three-dimensional color space.

The xy chromaticity plane, the uv chromaticity diagram and the u'v' chromaticity diagram provide two-dimensional separation of texture from color, while the other XYZ color spaces, the Lab color space and the like provide three-dimensional separation of texture from color. Accordingly, the terms of XYZ color space histogram and Lab color space histogram are defined distinctively from the term of xy chromaticity histogram.

The XYZ color space histogram and the Lab color space histogram are different from each other. Computation of the texture spread index in the Lab color space converts XYZ color data into Lab chromaticity data and computes the texture spread index from the converted data.

Any of various shifting techniques may be employed to bring one histogram distribution close to the other histogram distribution; for example, a technique of causing a predetermined position, for example, the center of one histogram distribution to match with the center of the other histogram distribution, a technique of bringing predetermined positions, for example, the respective centers of histogram distributions close to each other in a predetermined range, a technique of moving one histogram distribution in parallel to a coordinate axis to be close to the other histogram distribution, or a technique of linearly moving one center to be close to the other center. The amount of shift, the direction of shift and the like may be set appropriately, as long as such a shift provides an appropriate index.

The index is not limited to a two-dimensional form or a three-dimensional form but may be any of various forms, such as an index number, a graph, a graphic or any combination thereof.

According to one technically related aspect of the disclosure, there is provided a texture evaluation apparatus of a metal surface, comprising: a camera configured to have three spectral sensitivities ($S1(\lambda)$, $S2(\lambda)$, $S3(\lambda)$) linearly and equivalently converted to a CIE XYZ color matching function; an arithmetic processor configured to obtain and compute data by conversion of an image that has three spectral sensitivities and that is obtained by the camera into tristimulus values X, Y and Z in a CIE XYZ color system; and a lighting unit configured to illuminate a metal surface. The arithmetic processor is configured to: set a specified inspection area out of data obtained by imaging the metal surface; calculate an X value, a Y value and a Z value of each of pixels included in the inspection area with respect to an inspection plane and a reference plane as the metal surface, divide the inspection area into grids in xy coordinates, XYZ coordinates or Lab coordinates that respectively correspond to an xy chromaticity diagram, an XYZ chromaticity diagram or a Lab chromaticity diagram, and integrate number of pixels included in each grid with respect to the inspection plane and the reference plane, so as to create xy chromaticity histogram distributions, XYZ color space histogram distributions or Lab color space histogram distributions; and identify centers of the two xy chromaticity histogram distributions, the two XYZ color space histogram distributions or the two Lab color space histogram distributions of the inspection plane and the reference plane, and compute a texture spread index of the xy chromaticity histogram distribution, the XYZ color space histogram distribution or the Lab color space histogram distribution by shifting the center of one of the xy chromaticity histogram distributions, one of the XYZ color space histogram distributions or one of the Lab color space histogram distributions to be closer to the other xy chromaticity histogram distribution, the other XYZ color space histogram distribution or the other Lab color space histogram distribution.

According to another technically related aspect of the disclosure, there is provided a texture evaluation method of a metal surface using a camera configured to have three spectral sensitivities ($S1(\lambda)$, $S2(\lambda)$, $S3(\lambda)$) linearly and equivalently converted to a CIE XYZ color matching function. The texture evaluation method comprises: generating data by conversion of an image that has three spectral sensitivities and that is obtained by imaging with the camera under lighting into tristimulus values X, Y and Z in a CIE XYZ color system; setting a specified inspection area out of data obtained by imaging the metal surface; calculating an X value, a Y value and a Z value of each of pixels included in the inspection area with respect to an inspection plane and a reference plane as the metal surface, dividing the inspection area into grids in xy coordinates, XYZ coordinates or Lab coordinates that respectively correspond to an xy chromaticity diagram, an XYZ chromaticity diagram or a Lab chromaticity diagram, and integrating number of pixels included in each grid with respect to the inspection plane and the reference plane, so as to create xy chromaticity histogram distributions, XYZ color space histogram distributions or Lab color space histogram distributions; and identifying centers of the two xy chromaticity histogram distributions, the two XYZ color space histogram distributions or the two Lab color space histogram distributions of the inspection plane and the reference plane, and computing a texture spread index of the xy chromaticity histogram distribution, the XYZ color space histogram distribution or the Lab color space histogram distribution by shifting the center of one of the xy chromaticity histogram distributions, one of the XYZ color space histogram distributions or one of the Lab color space histogram distributions to be closer to the other xy chromaticity histogram distribution, the other XYZ color space histogram distribution or the other Lab color space histogram distribution.

The imaging device of the present disclosure images the reference plane and the inspection plane with three spectral sensitivities ($S1(\lambda)$, $S2(\lambda)$, $S3(\lambda)$, i.e., in three channels. The means employed for this purpose may be any of, for example, an optical filter, a dichromic mirror or a dichroic prism set to obtain such spectral sensitivities.

The spectral sensitivities ($S_1(\lambda)$, $S_2(\lambda)$, $S_3(\lambda)$) of the imaging device are bell-shaped curves that have single peaks and do not take negative values according to the CIE XYZ spectral characteristics, and are obtained by equivalent conversion under the conditions that the respective spectral sensitivity curves have an identical peak value and a minimum overlap. The curve of spectral characteristic $S_1$ has the peak wavelength of 582 nm, the half width of 523 to 629 nm and the 1/10 width of 491 to 663 nm. The curve of spectral characteristic $S_2$ has the peak wavelength of 543 nm, the half width of 506 to 589 nm and the 1/10 width of 464 to 632 nm. The curve of spectral characteristic $S_3$ has the peak wavelength of 446 nm, the half width of 423 to 478 nm and the 1/10 width of 409 to 508 nm.

Advantageous Effects

The present disclosure quantifies the texture such as gloss, glaze, irregularity and the like of the metal surface by the diffraction phenomenon of illumination light using an XYZ system camera. This configuration advantageously allows for accurate and efficient evaluation that is significantly close to the human visual recognition.

BRIEF DESCRIPTION OF DRAWINGS

FIG. 3A is a diagram illustrating an example using dichroic mirrors; FIG. 3B is a diagram illustrating an example using a filter turret; and FIG. 3C is a diagram illustrating an example using optical filters 22a, 22b and 22c microscopically applied on an imaging element 23;

FIG. 8A is a diagram illustrating an inspection area T in the arithmetic processor 3 according to Embodiment 1 of the present disclosure; FIG. 8B is an xy chromaticity diagram showing a chromaticity area K in the chromaticity diagram corresponding to the inspection area T; FIG. 8C is a diagram showing the chromaticity area K divided into grids G; FIG. 8D is a diagram showing an overlap of chromaticity in an xy two-dimensional chromaticity diagram; FIG. 8E is a diagram showing a minimum distribution; and FIG. 8F is a diagram showing one example of xy chromaticity histogram distribution;

DESCRIPTION OF EMBODIMENTS

Figure 1:
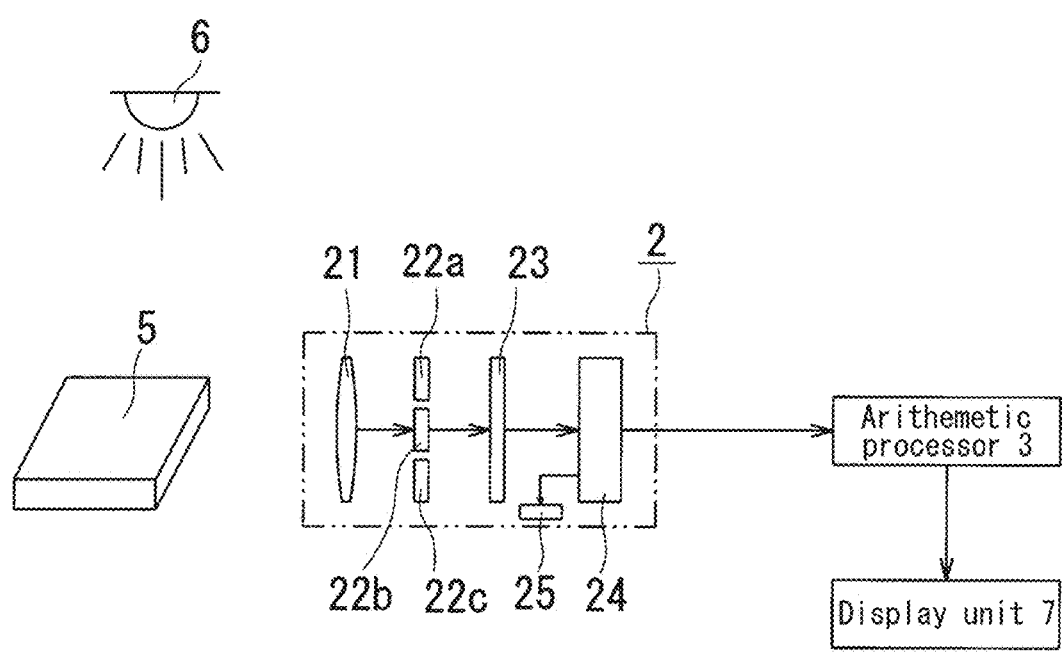
FIG. 1 is a block diagram illustrating a texture evaluation apparatus 1 of metal surface according to Embodiment 1 of the present disclosure.

A texture evaluation apparatus 1 of metal surface according to a preferable embodiment 1 of the present disclosure is described below with reference to FIGS. 1 to 10.

The surface texture evaluation apparatus 1 includes a two-dimensional colorimeter 2 configured to have three spectral sensitivities ($S1(\lambda)$, $S2(\lambda)$, $S3(\lambda)$) linearly and equivalently converted to a CIE XYZ color matching function, an arithmetic processor 3 configured to obtain and compute data by conversion of an image that has three spectral sensitivities and that is obtained by the two-dimensional colorimeter 2 into tristimulus values X, Y and Z in a CIE XYZ color system, and a lighting unit 6 configured to illuminate a metal surface 5. The arithmetic processor 3 sets a specified inspection area out of data obtained by imaging the metal surface 5, converts X, Y and Z values of each pixel in the inspection area into Lab values with regard to an inspection plane and a reference plane as the metal surface 5, and calculates respective average values of the Lab values. The arithmetic processor 3 subsequently divides the inspection area by grids in xy coordinates of an xy chromaticity diagram, integrates the number of pixels included in each grid with regard to the inspection plane and the reference plane, so as to create respective Lab color space histogram distributions, and identifies centers of two xy chromaticity histogram distributions of the inspection plane and the reference plane. The arithmetic processor 3 then shifts the center of one of the two xy chromaticity histogram distributions, an XYZ color space histogram distribution or an Lab color space histogram distribution to match with the center of the other xy chromaticity histogram distribution, and computes a width difference of the xy chromaticity histogram distribution, the XYZ color space histogram distribution or the Lab color space histogram distribution. The metal surface may be, for example, surface of a cutting tool, a mold or plating.

The flip-flop provides different views in different angles. The two-dimensional colorimeter 2 is manually moved for imaging in at least three different angles. The two-dimensional colorimeter 2 is placed below the lighting unit 6, and the angle of the two-dimensional colorimeter 2 is manually changeable. The metal surface 5 and its Lab color histogram distribution data are measurable in multiple different angles by the two-dimensional colorimeter 2.

Figure 2:
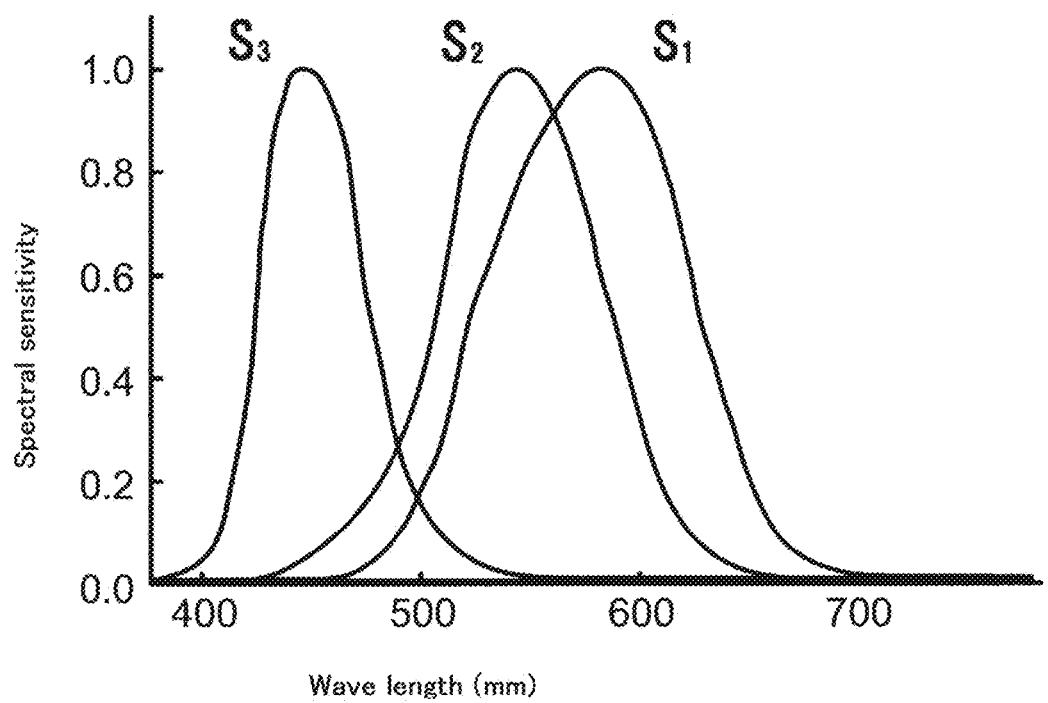
FIG. 2 is a graph showing spectral sensitivities of a two-dimensional colorimeter 2 that is an XYZ color system camera according to Embodiment 1 of the present disclosure.

The spectral sensitivities of the two-dimensional colorimeter 2 satisfy Luther condition. As shown in FIG. 2, the spectral sensitivities ($S1(\lambda)$, $S2(\lambda)$, $S3(\lambda)$) are converted equivalently from an XYZ color matching function on the conditions that spectral sensitivity curves take no negative values, are bell-shaped curves with single peaks, have an identical peak value and have a minimum overlap. More specifically the spectral sensitivities ($S1(\lambda)$, $S2(\lambda)$, $S3(\lambda)$) have the following characteristics:

|    | Peak Wavelength | Half Width | 1/10 Width |
|----|-----------------|------------|------------|
| S1 | 582 nm          | 523-629 nm | 491-663 nm |
| S2 | 543 nm          | 506-589 nm | 464-632 nm |
| S3 | 446 nm          | 23-478 nm  | 409-508 nm |

The peak wavelength of the spectral characteristic S1 may be regarded as 580±4 nm, the peak wavelength of the spectral characteristic S2 may be regarded as 543±3 nm, and the peak wavelength of the spectral characteristic S3 may be regarded as 446±7 nm.

The three spectral sensitivities ($S1(\lambda)$, $S2(\lambda)$, $S3(\lambda)$) are calculated according to Mathematical Expression 1 given below. Refer to, for example, JP 2005-257827A for the details of spectral characteristics.

$$\begin{bmatrix} S_1(\lambda) \\ S_2(\lambda) \\ S_3(\lambda) \end{bmatrix} = \begin{bmatrix} 0.51151 & 0.60975 & -0.10930 \\ -0.38668 & 1.16031 & 0.07538 \\ 0.0 & 0.0 & 0.56086 \end{bmatrix} \begin{bmatrix} \bar{x}(\lambda) \\ \bar{y}(\lambda) \\ \bar{z}(\lambda) \end{bmatrix} \quad \text{[Math. 1]}$$

The two-dimensional colorimeter 2 may be, for example, a two-dimensional colorimeter RC-500 manufactured by PaPaLab Co., Ltd. and has the specifications of the effective frequency of about 500 million pixels, the effective area of 9.93 mm×8.7 mm, the image size of 3.45 μm×3.45 μm, the video output of 12 Bit, the camera interface of GigE, the number of frames (at focusing) of 3 to 7 frames per sec, the shutter speed of 1/15,600 sec to 1/15 sec, the integration time of up to 3 seconds, the S/N ratio of not lower than 60 dB, F mount as the lens mount, the operation temperature of 0° C. to 40° C., and the operation humidity of 20% to 80%.

As shown in FIG. 1, the two-dimensional colorimeter 2 includes a photographic lens 21, three optical filters 22a, 22b and 22c placed behind the photographic lens 21 and an imaging element 23 (for example, CCD or CMOS) placed behind the optical filters 22a, 22b and 22c. The three spectral sensitivities ($S1(\lambda)$, $S2(\lambda)$, $S3(\lambda)$) of the two-dimensional colorimeter 2 are given as the products of spectral transmittances of the optical filters 22a, 22b and 22c and the spectral sensitivity of the imaging element 23. The positional relationship between the optical filters 22a, 22b and 22c and the imaging element 23 shown in FIG. 1 is only illustrative. The following describes specific methods of obtaining image information using the three spectral sensitivities ($S1(\lambda)$, $S2(\lambda)$, $S3(\lambda)$). Embodiment 1 may employ any of these methods or may employ another suitable method. An arithmetic unit 24 and a display unit 25 are also included in the two-dimensional colorimeter 2.

Figure 3A:
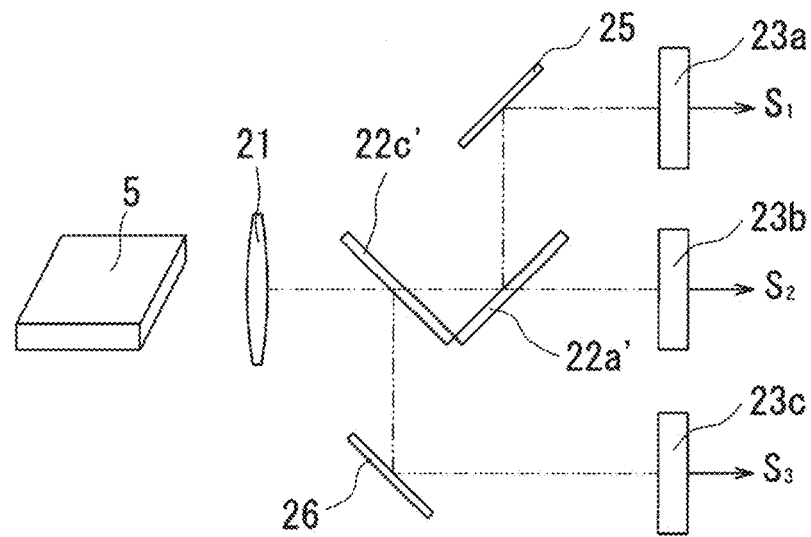
FIGS. 3A, 3B, and 3C are diagrams illustrating concrete examples of method of obtaining image information with three spectral sensitivities ($S1(\lambda)$, $S2(\lambda)$, $S3(\lambda)$) according to Embodiment 1 of the present disclosure.

FIG. 3A illustrates a method using dichroic mirrors. This method makes light of a specified wavelength reflected by a dichroic mirror 22c', disperses the transmitted light by making light of another specified wavelength reflected by another dichroic mirror 22a', and obtains information from three imaging elements 23a, 23b and 23c arrayed in parallel to one another. In this system, the dichroic mirror 22a' corresponds to the optical filters 22a and 22b, and the dichroic mirror 22c' corresponds to the optical filter 22c. With regard to incident light from a photographic lens 21, light of spectral sensitivity S3 is reflected by the dichroic mirror 22c', and the remaining light is transmitted. The light reflected by the dichroic mirror 22c' is reflected by a reflector 26, and the imaging element 23c provides spectral sensitivity S3. With regard to the light transmitted through the dichroic mirror 22c', on the other hand, light of spectral sensitivity S1 is reflected by the dichroic mirror 22a', and the remaining light of spectral sensitivity S2 is transmitted. The imaging elements 23a and 23b respectively provide spectral sensitivity S1 and spectral sensitivity S2. The dichroic mirrors may be replaced with a dichroic prism having similar characteristics to disperse light into three lights. Imaging elements 23a, 23b and 23c may be applied on the dichroic prism at positions where the respective lights are transmitted.

Figure 3B:
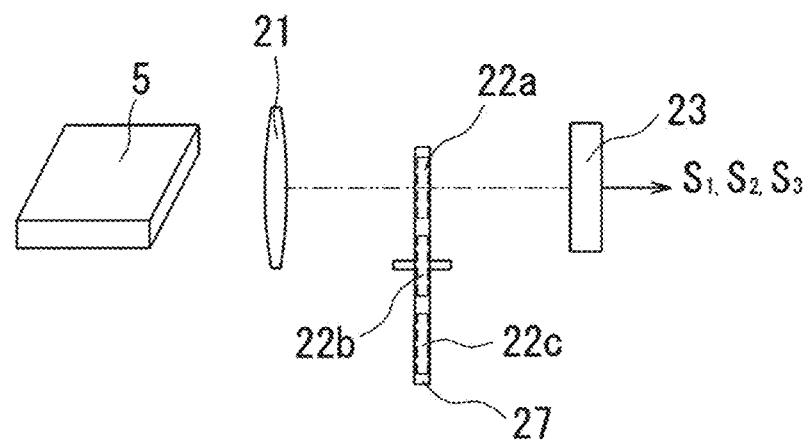

FIG. 3B illustrates a method using a filter turret 27. Optical filters 22a, 22b and 22c are provided on the filter turret 27 having an axis of rotation in a direction identical with the direction of incident light from a photographic lens 21 and are mechanically rotated. An imaging element 23 receives the sequentially transmitted lights and provides three spectral sensitivities S1, S2 and S3.

Figure 3C:
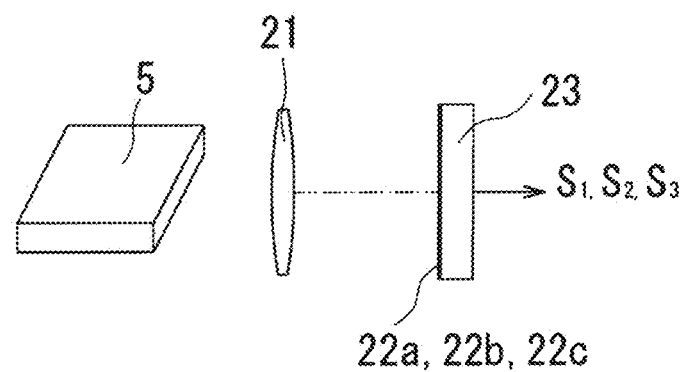

FIG. 3C illustrates a method using optical filters 22a, 22b and 22c microscopically applied on an imaging element 23. The optical filters 22a, 22b and 22c are provided in a Bayer array on the imaging element 23. In this array, the optical filer 22b is arranged in half of an area on the imaging element 23 in a grid pattern, and the optical filters 22a and 22c are arranged equally in respective halves of the remaining area. Accordingly, the layout ratio of the optical filter 22a: optical filter 22b: optical filter 22c=1:2:1. The array of the optical filters 22a, 22b and 22c is, however, not necessarily limited to the Bayer array according to Embodiment 1. The respective optical filters 22a, 22b and 22c are microscopic and are applied on the imaging element 23 by printing. The invention is, however, not characterized by this array but is characterized by application of filters characteristic of spectral sensitivities ($S1(\lambda)$, $S2(\lambda)$, $S3(\lambda)$) on an imaging element.

The two-dimensional colorimeter 2 sends image information obtained with the spectral sensitivities ($S1(\lambda)$, $S2(\lambda)$, $S3(\lambda)$) to the arithmetic processor 3. The arithmetic processor 3 converts the image information into tristimulus values X, Y and Z in the XYZ color system and performs an arithmetic operation by conversion of the obtained image data of the tristimulus values X, Y and Z. The arithmetic processor 3 includes a display unit (not shown) configured to display a visualized image.

The arithmetic processor 3 computes and visualizes the luminance, the chromaticity and the like at any position in the image obtained by the two-dimensional colorimeter 2. The metal surface 5 is obliquely irradiated with light. The arithmetic processor 3 compares and indexes the xy, the XYZ or the Lab chromaticity distribution data of the metal color.

The two-dimensional colorimeter 2 generally images the metal surface 5 at one location, and may be moved to image the metal surface 5 at a different angle as needed basis. For example, the metal surface 5 may be imaged at three different locations (any adequate number of locations) such as at the front, 45 degrees left and 45 degrees right.

A xenon lamp (simulated solar light) is employed as the light source of the lighting unit 6. The lighting unit 6 includes a Fresnel lens assembly, in addition to the xenon lamp. The metal surface 5 is uniformly irradiated obliquely downward with the xenon lamp. The xenon lamp may be replaced with an LED artificial sunlight lamp. The natural solar light may be used as a lighting source.

A display unit 7 is connected with the arithmetic processor 3 and is configured to receive an image signal processed by the arithmetic processor 3 and display an image on the screen. The arithmetic processor 3 or the display unit 7 adequately includes an input unit (not shown). The input unit may be, for example, a keyboard, a mouse or a touch panel provided on an image display device.

Figure 4:
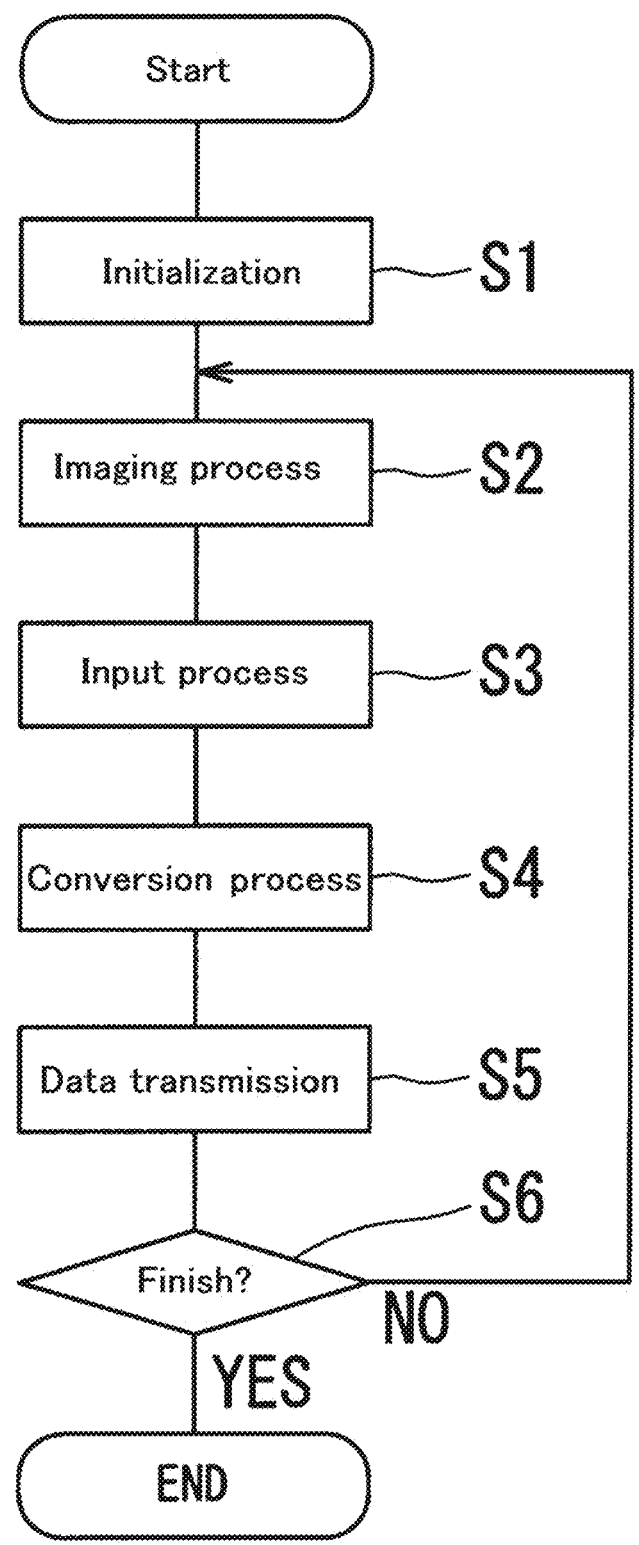
FIG. 4 is a flowchart showing a processing flow performed by the two-dimensional colorimeter 2 according to Embodiment 1 of the present disclosure.
Figure 6:
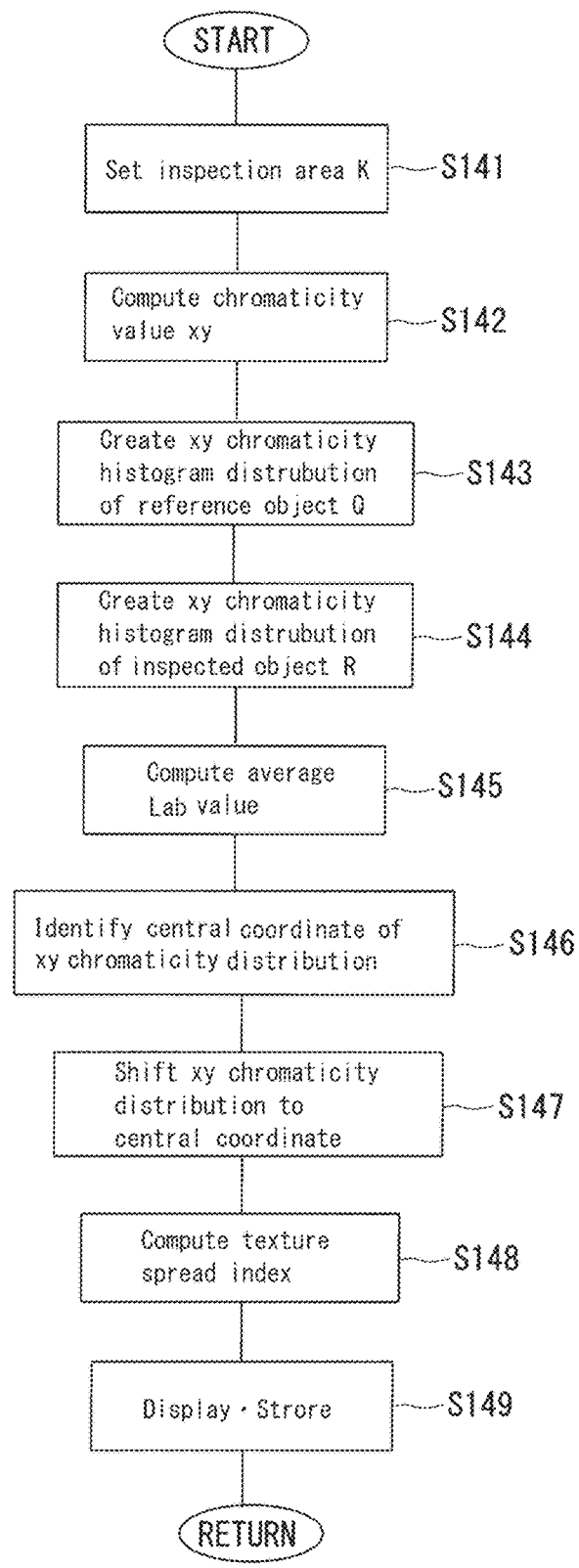
FIG. 6 is a sub-flowchart showing a sub-flow by the arithmetic processor 3 according to Embodiment 1 of the present disclosure.

The following describes the operations of the texture evaluation apparatus 1 of the metal surface 5 with reference to a concrete example. As shown in FIG. 1, the texture evaluation apparatus 1 of the metal surface 5 is operated by connection of the two-dimensional colorimeter 2, the arithmetic processor 3 and the display unit 7. The method of connection may be freely selectable among various wired and wireless connection techniques. FIG. 4 is a flowchart showing a processing flow performed by the two-dimensional colorimeter 2, and FIG. 6 is a flowchart showing a processing flow performed by the arithmetic processor 3.

As shown in FIG. 4, when being powered on, the two-dimensional colorimeter 2 is initialized (initialization S1). The two-dimensional colorimeter 2 takes an image of the metal surface 5 with the spectral sensitivities (S1($\lambda$), S2($\lambda$), S3($\lambda$)) (imaging process S2), subsequently inputs the taken image data by means of the imaging element 23 (input process S3), and converts the input data into tristimulus values X, Y and Z by the arithmetic processor 3 (conversion process S4). The spectral sensitivities (S1($\lambda$), S2($\lambda$), S3($\lambda$)) are sent to the display unit 7 (data transmission S5). When the image is a moving image, the series of processing from the imaging process S2 to the data transmission S5 is performed continuously. The image is displayed on the image display unit 7.

In the imaging process S2, any of various metal surfaces 5 may be measured. The metal surface 5 is imaged with the two-dimensional colorimeter 2 at different angles with regard to a specified area in different imaging locations. There are a plurality of imaging locations, and any adequate number of imaging locations may be selected. For example, the metal surface 5 is measured in three different directions, i.e., at the front (0 degree), 45 degrees left and 45 degrees right. At the measurement location, the optical axis of the two-dimensional colorimeter 2 at 0 degree is perpendicular to the metal surface 5. Lighting is characterized by obliquely downward lighting like the sunlight.

For the purpose of reference, conversion equations from the tristimulus values X, Y and Z into a Y'xy color system are given as Mathematical Expressions 2 and 3. A luminance meter (not shown) is used together with the two-dimensional colorimeter 2, and the value Y is corrected with a value (nt) of the luminance meter to Y'. The conversion equations in the color space are commonly used, so that the other equations are not specifically shown.

The XYZ color system is currently used as a CIE standard color system and is the basis of the respective color spaces. The XYZ color system is developed based on the principle of additive mixture of three primary colors of light (R=red, G=green and B=blue) and expresses each color by three values Y, x and y using the chromaticity diagram. Y denotes the reflectance and corresponds to the brightness, and x and y denote chromaticities.

$$x = \frac{X}{X+Y+Z} \quad \text{[Math. 2]}$$

$$y = \frac{Y}{X+Y+Z} \quad \text{[Math. 3]}$$

The imaging process S2 is a process of imaging the metal surface 5 with the two-dimensional colorimeter 2 having the three spectral sensitivities (S1($\lambda$), S2($\lambda$), S3($\lambda$)) (as shown in FIGS. 1 and 4). The spectral sensitivities (S1($\lambda$), S2($\lambda$), S3($\lambda$)) are given by above Mathematical Expression 1. The input process S3 is concurrently and sequentially performed with imaging using the photographic lens 21, the optical filters 22a, 22b and 22c and the imaging element 23.

The input image data are values according to the spectral sensitivities (S1($\lambda$), S2($\lambda$), S3($\lambda$)). The arithmetic processor 3 performs the conversion process S4 to convert the image data of the image taken by the two-dimensional colorimeter 2 into tristimulus values X, Y and Z. This conversion is performed according to Mathematical Expression 1. More specifically, tristimulus values X, Y and Z are obtained by multiplication of an inverse matrix of the coefficients in Mathematical Expression 1. The two-dimensional colorimeter 2 sends the values according to the spectral sensitivities (S1($\lambda$), S2($\lambda$), S3($\lambda$)) to the arithmetic processor 3.

Figure 5:
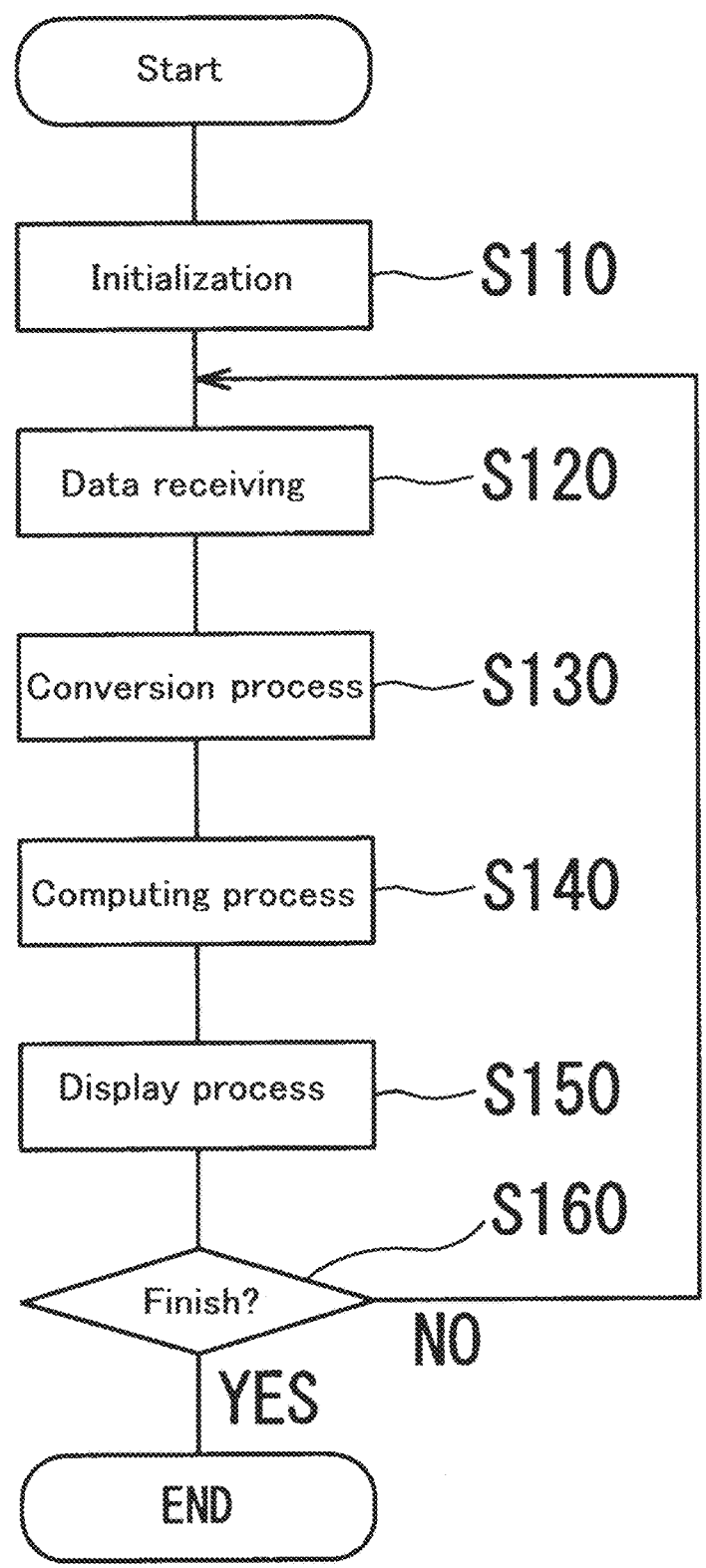
FIG. 5 is a flowchart showing a processing flow by an arithmetic processor 3 according to Embodiment 1 of the present disclosure.

As shown in FIG. 5, when being powered on, the arithmetic processor 3 is initialized (initialization S110). In the state that the display unit 7 is connected with the two-dimensional colorimeter 2, the arithmetic processor 3 receives the spectral sensitivities (S1($\lambda$), S2($\lambda$), S3($\lambda$)) sent from the two-dimensional colorimeter 2 (data receiving S120). The arithmetic processor 3 subsequently converts the spectral sensitivities (S1($\lambda$), S2($\lambda$), S3($\lambda$)) into tristimulus values X, Y and Z (S140) and sends the result of computation to the display unit 7 (display process S150). In response to the data receiving S120 from the two-dimensional colorimeter 2, the series of processing from the conversion process S130 to the display process S150 is performed continuously.

The computation process S140 is a process of computing and visualizing Lab average values and xy texture spread indexes of the taken images with regard to the reference plane and the inspection plane. Color information may be converted into, for example, RGB data as required for display on the display unit 7.

The display process S150 is a process of displaying the visualized texture spread indexes on the image display device. The processing flow then goes to return.

The following describes the details of the process S140 with reference to a sub-flowchart of FIG. 6. The process takes a first image (image B) of the reference plane, takes a second image (image A) of the inspection plane to be compared, and sequentially calculates the texture spread indexes as described below. The texture spread indexes that separate the texture are used to identify the similarity of texture.

The process sets an inspection area K (shown in FIG. 8B) corresponding to a target area T to be inspected (shown in FIG. 8A) with regard to obtained images A and B (step S141). The size and the location of the inspection area K may be set arbitrarily.

The process computes the chromaticities xy and determines the chromaticities Yxy (S142).

The process creates an xy chromaticity histogram distribution of the inspection plane in the area K cut out from the taken image A of the inspection plane (S143). This chromaticity histogram distribution shows an integrated number of pixels included in an overlap area D of two histogram distributions shown in FIG. 8D.

The xy chromaticity histogram distribution is a three-dimensional histogram showing an integrated number of pixels included in each of the unit grids described above, and the overlap area D is shown in FIG. 8D.

FIG. 8C shows a plane of color distribution for comparison at the positions of xy coordinates. The inspection area K is divided into grids G, and a histogram distribution is created by integrating the number of pixels having the xy values in each divisional area with respect to the z axis. Each divisional area is a plane grid by dividing the xy coordinates in grids of a specific width (three-dimensional grids), for example, by dividing xy coordinates into 1000 (by 1000 lines). The histogram is scanned from one end to the other end. The number of pixels included in each divisional area divided as the grid G is scanned in an identical xy plane and is integrated in the z direction. Computing the xy coordinates in only a specified range with regard to the inspection area K shortens the computation time. Using the smaller grids increases the accuracy but also increases the computation time. Accordingly, grids of adequate size are to be used.

Like S143, the process creates an xy chromaticity histogram distribution with regard to the image B of the reference plane (S144). In the xy chromaticity histogram distribution, the xy axes shows xy chromaticities and the z axis shows the integrated number of pixels. FIG. 8D shows an overlap area in two dimensions.

The process individually sums the values of the L axis, the a axis and the b axis in the Lab space with regard to all the pixels included in the inspection area and divides the respective sums of the L value, the a value and the b value by the total number of pixels. This calculates an average L value, an average a value and an average b value in the Lab chromaticity distribution (S145).

The process calculates the Lab values in the Lab space converted by Mathematical Expression 4 given below. The Lab color space is a type of complementary color space and has a dimension L representing the brightness and complementary color dimensions A and B. This is based on the nonlinearly compressed coordinates in a CIE XYZ color space. The XYZ values prior to normalization are converted into Lab values by Mathematical Expression 4. This provides a distribution in the Lab color space by addition in the brightness direction to the distribution in the XYZ color space.

$$f(t) = \begin{cases} t^{1/3} & \text{When } t > (6/29)^3 = 0.008856\ldots \\ [(29/3)^3 t + 16]/116 & \text{Otherwise} \end{cases}$$

$$L^* = 116 f(Y/Y_n) - 16$$
$$a^* = 500[f(X/X_n) - f(Y/Y_n)]$$
$$b^* = 200[f(Y/Y_n) - f(Z/Z_n)]$$

[Math. 4]

In Mathematical Expression 4, the values X, Y and Z are respectively divided by coordinates Xn, Yn and Zn of a neutral point in the parentheses of the function f, in order to adjust their maximum values to 1.

Differences of the average values of the reference plane and the inspection plane are calculated and are used as the criteria for determination of color difference.

Figure 7:
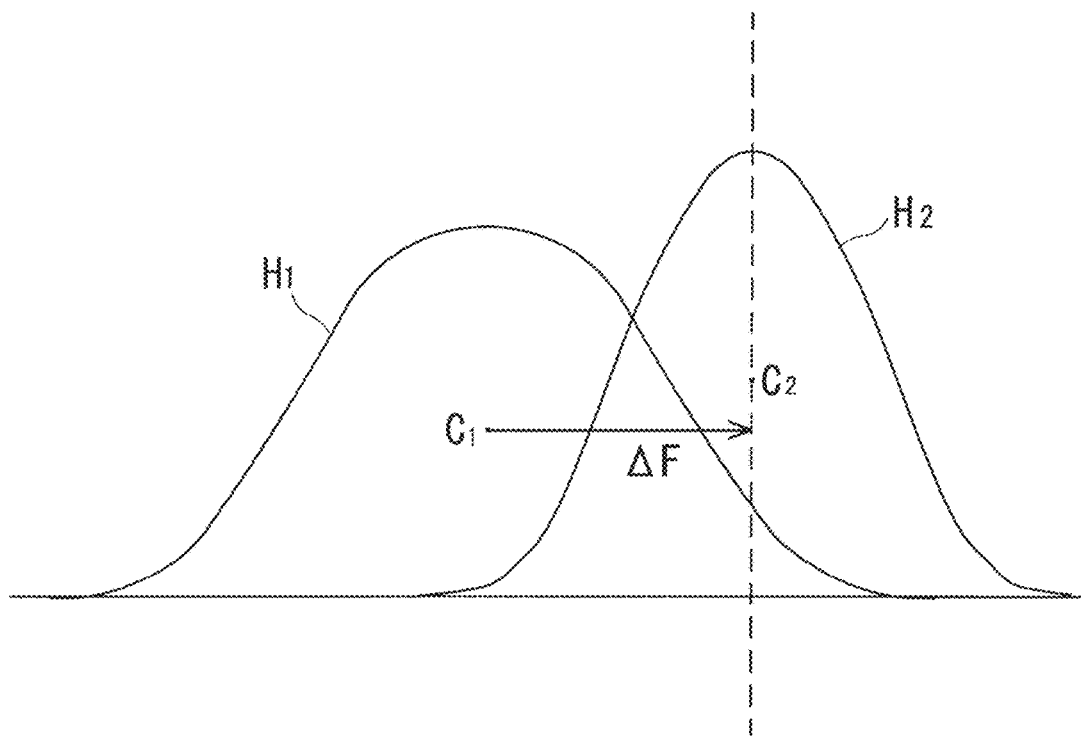
FIG. 7 is a diagram illustrating a shift process in an xy coordinate space by the arithmetic processor 3 according to Embodiment 1 of the present disclosure.

The process identifies central coordinates C1 and C2 in the xy chromaticity distribution (S146) as shown in FIG. 7. The central coordinate herein denotes a centroid (center of gravity).

The process shifts (maps) the entire xy chromaticity distribution by a deviation ΔF of the central coordinate, such that one of central coordinates of two xy histogram distributions $H_1(x,y)$ and $H_2(x,y)$ matches with the other central coordinate (S147) as shown in FIG. 7. A difference in color component is calculated without such a shift of one distribution to the other distribution. The distribution may be shifted on the graph or may be shifted by calculation. The amount of the shift may be set appropriately. A shift of one center into a predetermined range around the other center has similar effects as those of a shift of one center to the other center. There is accordingly a need to bring the two distributions closer to each other by an appropriate amount of shift that enables the texture to be evaluated.

The process computes a texture spread index that indicates a spatial spread difference (S148). This computation simply extracts a difference in metallic degree, separates the metallic degree from the similarity of chromaticity, and determines and quantifies the metallic degree. This computation computes the spread in the two-dimensional space of xy chromaticity distribution and recognizes a difference in spread as a difference in glitter between glitter materials excluding the color. This accordingly enables the texture to be accurately detected separately from the color.

The texture spread index is calculated by an expression given below. The xy chromaticity histogram distribution indicates an integrated number of pixels. FIG. 8D shows an overlap area D, and FIG. 8E shows a minimum distribution.

texture spread index=integrated number of pixels included in overlap area D/total number of pixels in inspection area K×100(%)

The process calculates spread histograms of the reference plane and the inspection plane on the two-dimensional space and takes a minimum value in the spread histograms at an identical position as an overlap frequency. The overlap frequency is divided by the total number in the entire histogram.

FIGS. 8D and 8E show one cross section taken on an S-S line of FIG. 8C. There is an overlap in the xy coordinates on the same line. As a matter of convenience, the cross section is shown in two dimensions, instead of three dimensions. The histogram has a distribution in a small step-like shape. An integrated number $H_1$ and an integrated number $H_2$ in FIG. 8D respectively correspond to the image A and the image B. Comparison of the two histogram distributions provides an overlap area D.

In FIG. 8E, $H_1(x_1,y_1)$ denotes an integrated number of the xy chromaticity histogram distribution of the inspection plane, and $H_2(x_1,y_1)$ denotes an integrated number of the xy chromaticity histogram distribution of the inspection plane. In a left side area of the overlap area, $H_1 > H_2$. In the overlap area, $H_1 = H_2$. In a right side area, $H_1 < H_2$. The smaller integrated number (pixel frequency) between $H_1$ and $H_2$ is $H_1$ in the left side area and $H_2$ in the right side area. This provides a minimum distribution that is a step-like histogram curve. The ratio of the overlap area D to the overall area may be calculated by using this minimum distribution.

The smaller integrated number is specified in this minimum distribution. The integrated number in the overlap area D is calculated by summing up the smaller integrated number between $H_1$ and $H_2$. The ratio to the total number of pixels is then determined. The total number of pixels in the inspection area K is fixed. The inspection plane and the reference plane have an identical total number of pixels. This ratio may be integrated three-dimensionally with regard to all the grids G. In another example, as shown in FIG. 8C, the distribution of the integrated number of pixels may be integrated two-dimensionally, for example, by cutting the inspection area K along the S-S line and changing the value x from one end to the other end while fixing the value y to a predetermined value. FIG. 8F is a two-dimensional map showing the results of integration on the xy coordinates. The inspection area K having no distribution and having the pixel number of zero is excluded from the computation.

The process then performs the display and storage process and the transmission process (S149) and goes to Return.

For example, it is assumed that the number of pixels included in the inspection area K is 100 pixels in length×100 pixels in width=10,000 pixels. Corresponding inspection areas K are cut from the respective images, so that both the image A and the image B have the same total number of pixels, i.e., 10,000 pixels. The number of pixels in the overlap area is integrated from the xy chromaticity histogram. The integrated number of 5,000 indicates the texture spread index of 50%. The degree of difference in texture increases with a decrease in texture spread index from 100%. The texture spread index of 100% indicates the complete consistency of the distribution of the xy values. The texture spread index of or above a predetermined value is evaluated as the plane of texture conformance.

The color information obtained primarily from an image is three spectral sensitivities (S1(λ), S2(λ), S3(λ)) by a function equivalent to an XYZ color matching function. Compared with color information in RGB, this color information is more faithful to the sensitivity of human eye and the higher accuracy. This provides a small overlap of the spectral sensitivities (S1(λ), S2(λ), S3(λ)) and a sufficiently high S/N ratio, and natural changes in curves of spectral sensitivities. This accordingly minimizes the error in colorimetry.

The texture of the image may be recognized separately from the color by the histogram distribution. Even the subtle color difference is thus determinable by reflecting the differences of gloss, glaze, irregularity, roughness and the like of the surface.

Figure 9A:
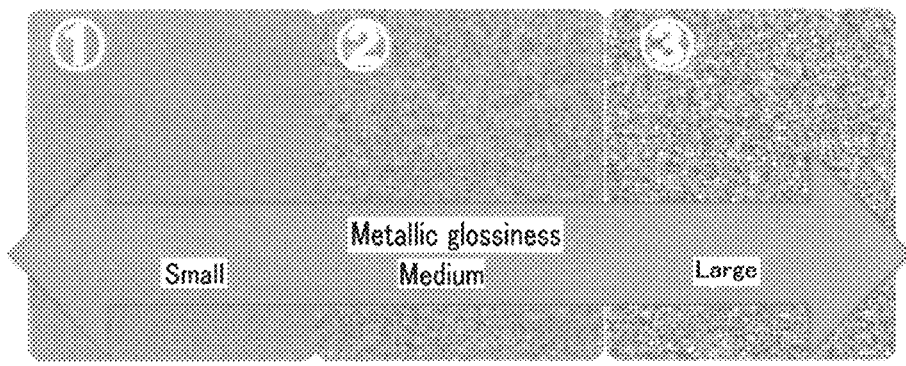
FIG. 9A is a diagram showing the metallic degrees of metal surfaces.
Figure 9B:
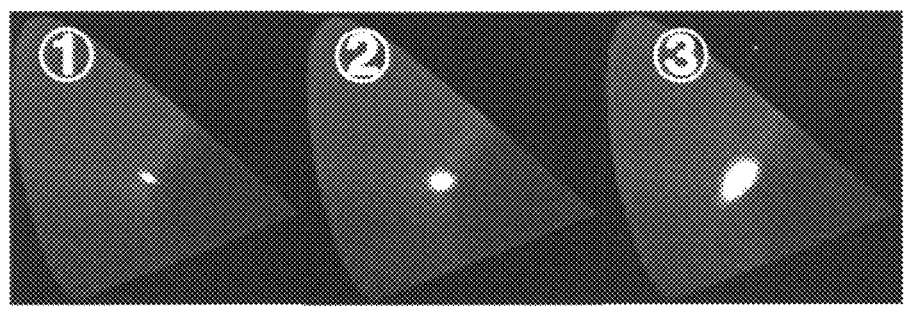
FIG. 9B is a diagram showing xy chromaticity histogram distributions.
Figure 9C:
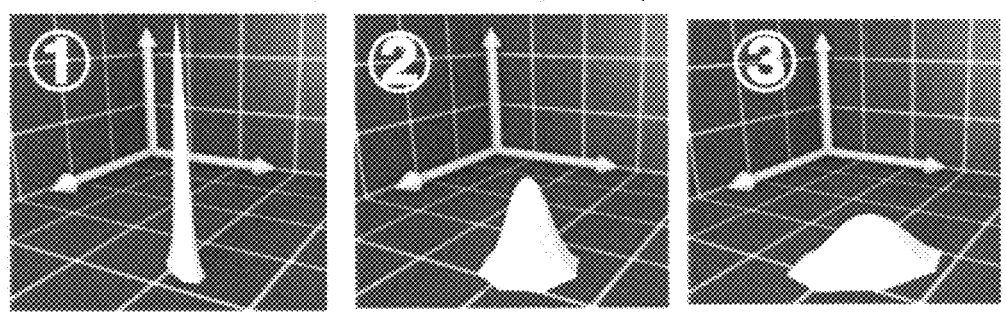
FIG. 9C is a three-dimensional image diagram showing xy chromaticity histogram distributions.

The following describes an example of inspecting three different planes having different levels of metallic texture with reference to FIGS. 9A to 9C. A plane having the lowest level of metallic texture is specified as a reference plane 1, a plane having the medium level of metallic texture is specified as an inspection plane 2, and a plane having the highest level of metallic texture is specified as an inspection plane 3. Distributions of the respective planes 1 to 3 that are subjected to the above series of processing are created in the xy chromaticity diagram. As shown in the xy chromaticity diagram of FIG. 9B, these distributions are given as data of integration of the highlighted areas. The integrated number is expressed by brightness. The brighter color indicates the larger integrated number. FIG. 9C schematically illustrates the integrated numbers of the reference plane and the inspection planes in three dimensions. The xy axes show the chromaticities, and the z axis shows the integrated number. The higher metallic texture basically provides a lower and wider peak, and the lower metallic texture provides a sharper peak. A texture spread index indicating an overlap degree is computed by comparing two histograms of the reference plane 1 and the inspection plane 2 or 3.

As shown in Table 1, a comparative example uses Lab values calculated as average values of color having ΔE as the basis of texture. This provides only small differences in Lab values and ΔE compared with the visual recognition, and thereby leads to a difficulty in inspection. The texture spread index of this embodiment, however, directly uses an integrated number in the range of the inspection area K. The texture spread indexes of the inspection plane 2 and the inspection plane 3 relative to the reference plane 1 are respectively 80% and 30%. This allows for the clear and easy numerical discrimination of the metallic texture.

TABLE 1

Comparative inspection example of reference plane (1) and inspection plane (2), (3)

| | L value | a value | b value | ΔE | Texture spread index |
|---|---|---|---|---|---|
| (1) | 50.40 | −1.96 | 10.60 | — | — |
| (2) | 50.52 | −1.97 | 10.21 | 0.121 | |
| (3) | 51.13 | −1.96 | 10.45 | 0.740 | 30% |

A texture evaluation apparatus 101 of a metal surface 105 according to Embodiment 2 is described below with reference to FIG. 10, FIG. 11 and FIG. 12. Like elements are expressed by like numerals in 100s and are not specifically described. The following mainly describes the differences.

The texture evaluation apparatus 101 includes a two-dimensional colorimeter 102 configured to take images of a reference plane and an inspection plane, an arithmetic processor 103 connected with the two-dimensional colorimeter 102 via a switch 106 and configured to receive signals and compute a texture spread index, and a display unit 107 connected with the arithmetic processor 103 and configured to display the index.

Figure 10:
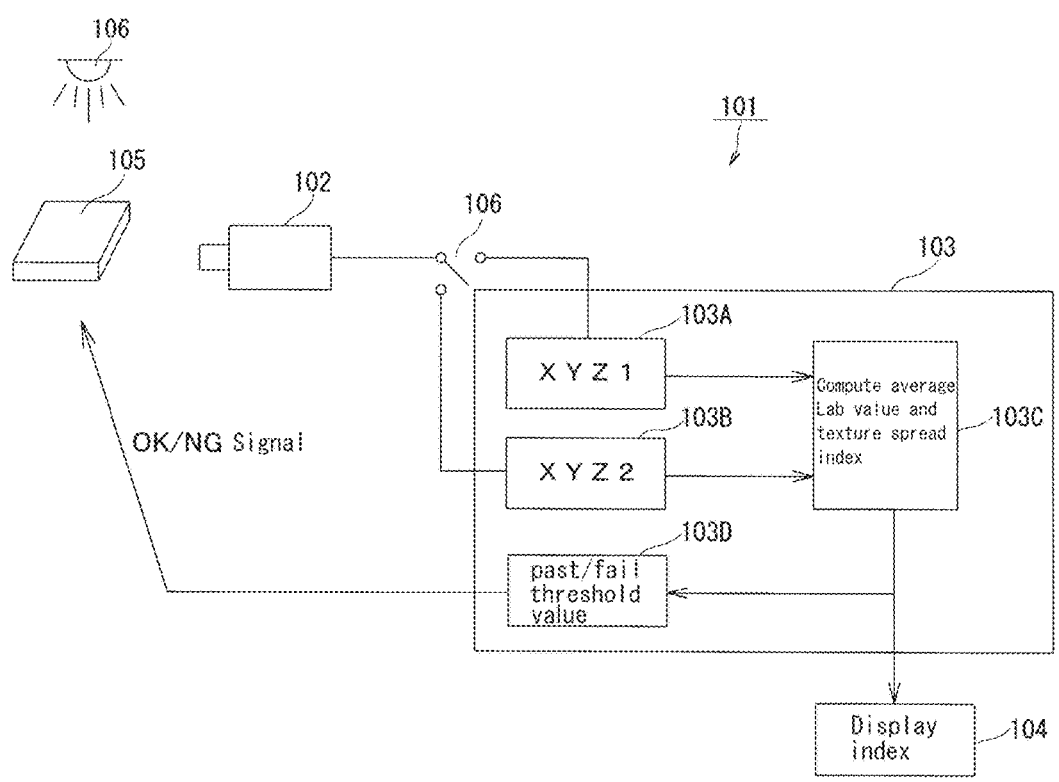
FIG. 10 is a block diagram illustrating the configuration of a texture evaluation apparatus 101 of metal surface according to Embodiment 2 of the present disclosure.

As shown in FIG. 10, the arithmetic processor 103 includes an operator 103A configured to compute stimulus values XYZ1 obtained by imaging the color sample as a reference plane, an operator 103B configured to compute stimulus values XYZ2 obtained by imaging a color sample as an inspection plane, and an operator 103C connected with the operator 103A and the operator 103B and configured to compute a texture spread index of the metal surface 105. An OK signal or an NG signal from the operator 103C is sent to the display unit 107 or is sent to the outside. The switch 106 is configured to selectively input the stimulus values XYZ1 or the stimulus values XYZ2.

Figure 11:
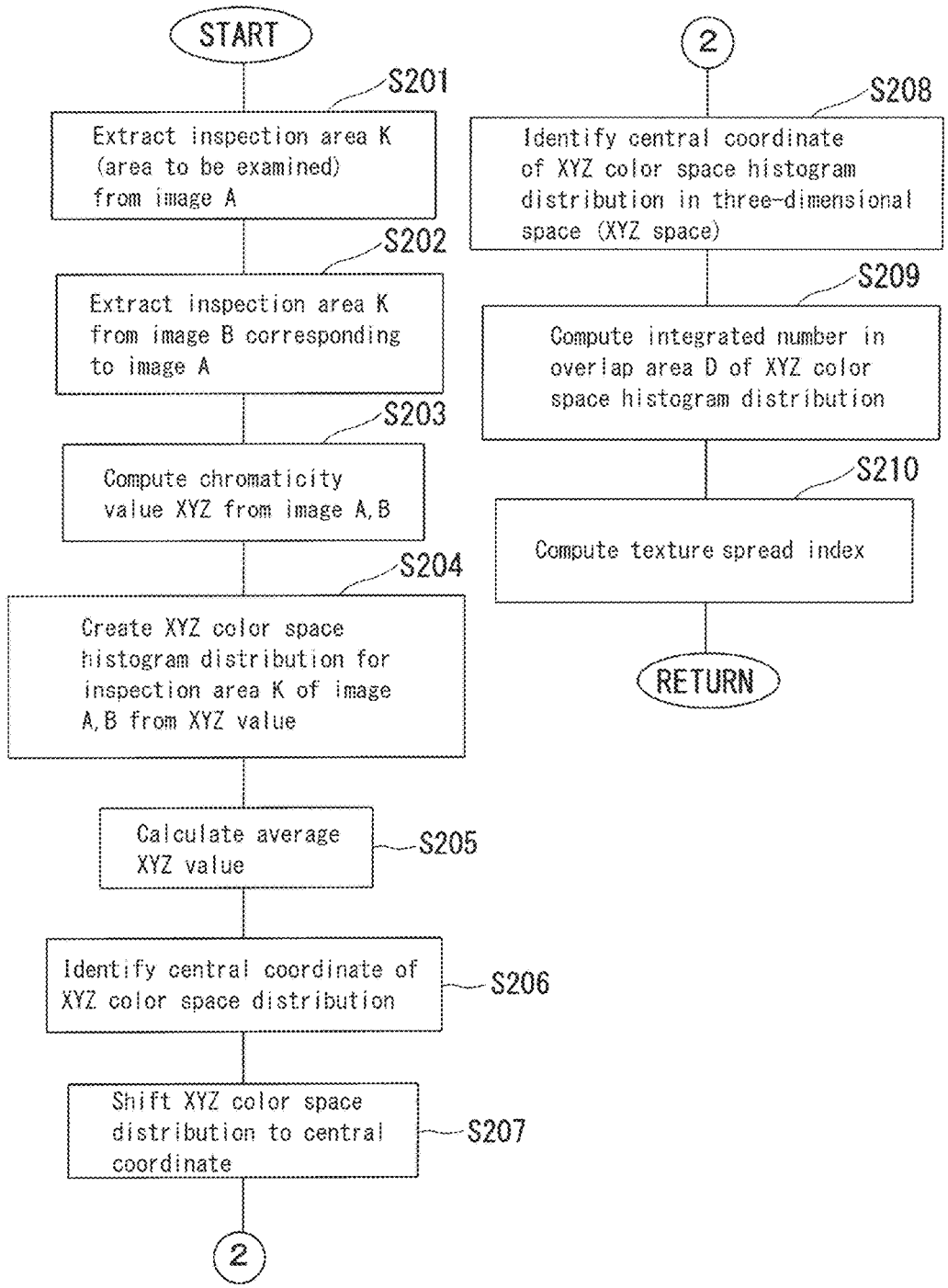
FIG. 11 is a flowchart showing a processing flow (XYZ color space distribution) performed by an arithmetic processor 103 in the texture evaluation apparatus 101 of metal surface according to Embodiment 2 of the present disclosure.

FIG. 11 is a flowchart showing a process of computing the texture spread index by comparison of chromaticity histogram distributions of two images A and B. As shown in FIG. 11, when the program is triggered, the process extracts, specifies and sets an inspection area K from the image A (S201). The process subsequently extracts, specifies and sets an inspection area corresponding to that of the image A from the image B (S202). The process computes chromaticity values XYZ from the images A and B (S203). The process respectively computes and creates XYZ color space histogram distributions of the inspection plane and the reference plane with regard to the inspection area K (S204). The process subsequently calculates average values of the XYZ values (S205), identifies a central coordinate of an XYZ color space distribution (S206), and shifts the XYZ color space distribution to the central coordinate (S207). After the shift process, the process identifies a central coordinate of the XYZ color space distribution (S208). This aims to check the suitability of the central coordinate after the shift process. The central coordinate may be readjusted as needed. The process subsequently identifies a minimum distribution of the XYZ color space histogram distributions and computes an integrated number in an overlap area D of the XYZ color space histogram distributions (S209). The texture spread index is given as (integrated number of pixels included in the overlap area D/total number of pixels in the inspection area K)×100(%). The smaller integrated number between $T_1$ and $T_2$ is summed up as the integrated number in the overlap area D. The process computes the texture spread index (S210) and goes to Return.

Figure 13A:
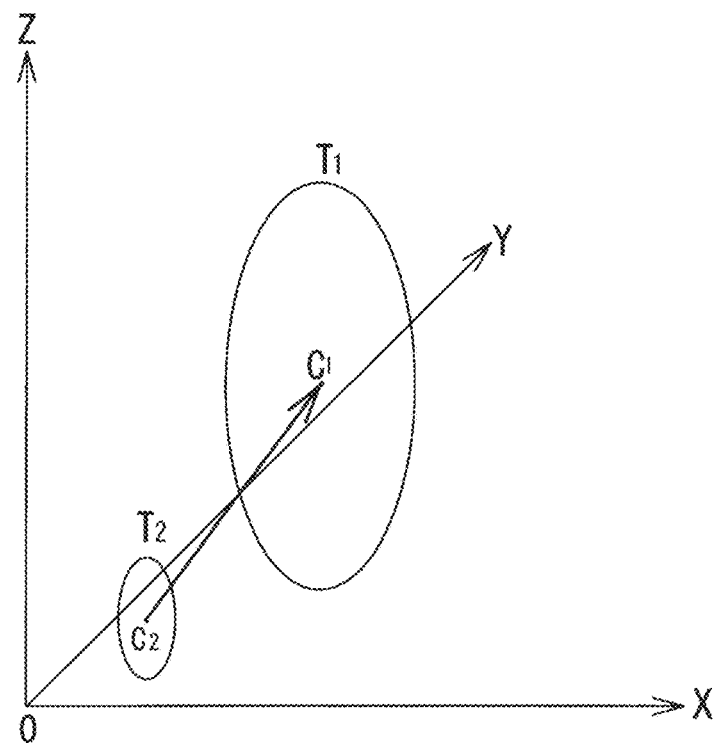
FIGS. 13A and 13B are diagrams illustrating a shift process in an xy coordinate space performed by the texture evaluation apparatus 101 of metal surface according to Embodiment 2 of the present disclosure.
Figure 13B:
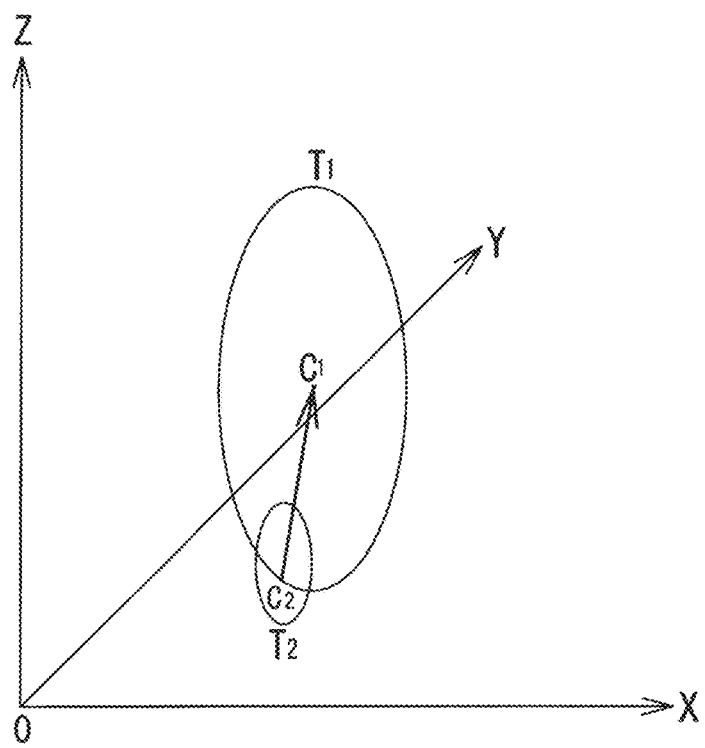

In computation of an XYZ distribution corresponding to the inspection area K, the index is computed, based on distributions of an X axis, a Y axis and a Z axis in a three-dimensional space. As shown in FIGS. 13A and 13B, $T_1(X,Y,Z)$ and $T_2(X,Y,Z)$ respectively denote XYZ values of the inspection plane and the reference plane in XYZ space coordinates. In the XYZ color space, each histogram distribution has a globe-like shape. Two histogram distributions may be three-dimensionally overlapped or may be three-dimensionally separated from each other. The respective central coordinates are brought closer to each other by a shift process. The inspection area K in the three-dimensional space is divided into grids. Three-dimensional chromaticity histogram distributions of $T_1(X,Y,Z)$ and $T_2(X,Y,Z)$ and minimum distribution are determined, and the index is computed similarly. An integrated number of grids may be projected on a plane, and an integrated number in an overlap area in the plane on the grids by similar integration. The XYZ chromaticity does not include brightness information, so that the histogram distribution does not change with a change in brightness of the image in the XYZ space.

Figure 12:
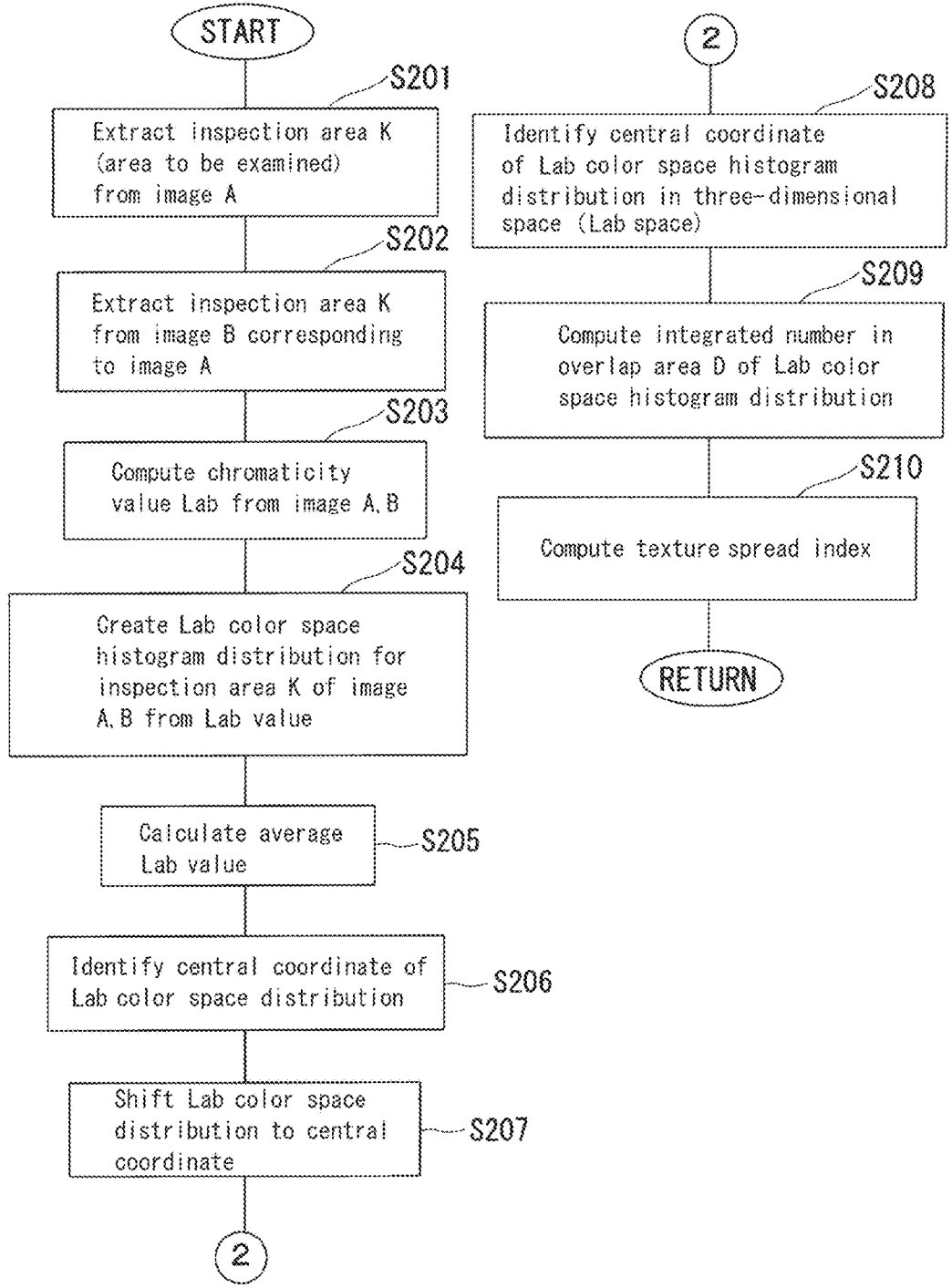
FIG. 12 is a flowchart showing a processing flow (Lab color space distribution) performed by the arithmetic processor 103 in the texture evaluation apparatus 101 of metal surface according to Embodiment 2 of the present disclosure.

Instead of the XYZ color space histogram, an Lab color space histogram may be used for evaluation of texture with reference to the flowchart of FIG. 12. The above description of FIG. 11 is generally applicable to the description of FIG. 12. In FIG. 12, the process calculates average Lab values of the inspection area of the image A and average Lab values of the inspection area of the image B at S205. The Lab chromaticity includes brightness information, so that the histogram distribution changes with a change in brightness of the image in the Lab space.

Figure 14:
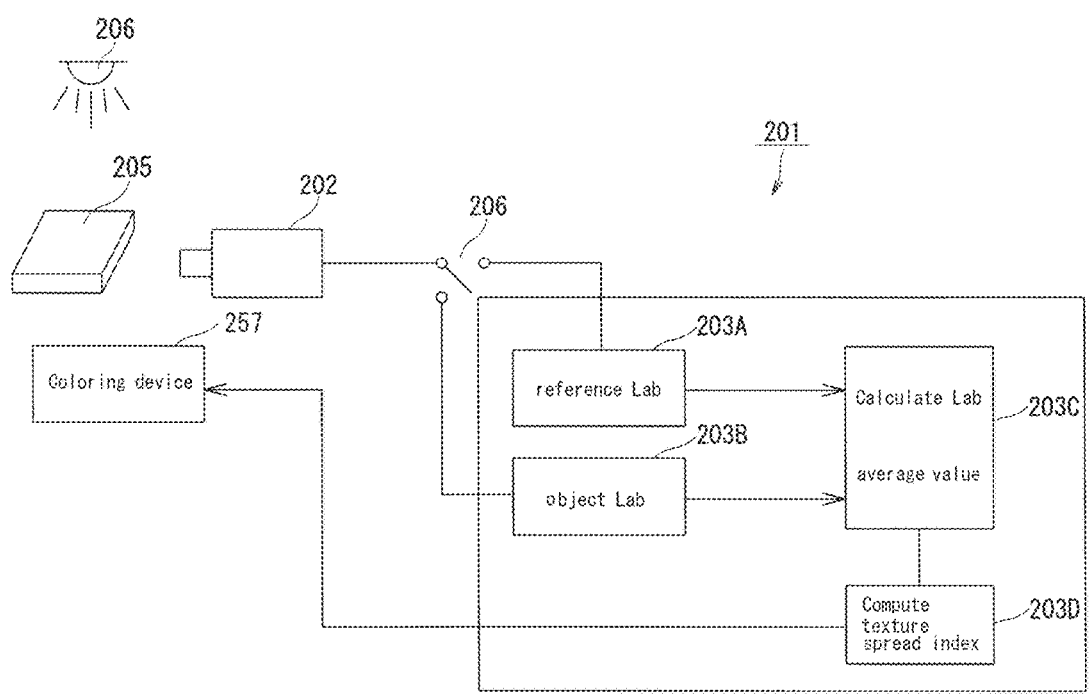
FIG. 14 is a block diagram illustrating the configuration of a texture evaluation apparatus 201 of metal surface according to Embodiment 3 of the present disclosure.

The following describes a texture evaluation apparatus 201 of a metal surface 205 according to Embodiment 3 with reference to FIG. 14. Like elements are expressed by like numerals in 200s and are not specifically described. The following mainly describes the differences.

As shown in FIG. 14, a color determination object is a partial area of the metal surface 205, and a two-dimensional colorimeter 202 is used to image an object area of the metal surface 205. An arithmetic processor 203 includes an operator 203A configured to calculate Lab values from stimulus values XYZ1 as a reference, an operator 203B configured to calculate Lab values from stimulus values XYZ2 as a determination object, an operator 203C connected with the operator 203A and the operator 203B and configured to calculate Lab average values, and a texture spread index operator 203D configured to compute a texture spread index from the reference Lab values and the object Lab values. The arithmetic processor 203 sends the computed values from the operators 203C and the 203D to a coloring device 257. The coloring device 257 determines whether the metallic texture is appropriate, based on the index value, with checking the image and additionally performs a coloring process. A switch 206 is used to selectively input either the reference XYZ values and the object XYZ values. The primary processing flow is approximately similar to the flowcharts of Embodiments 1 and 2 and is not specifically described.

Figure 15A:
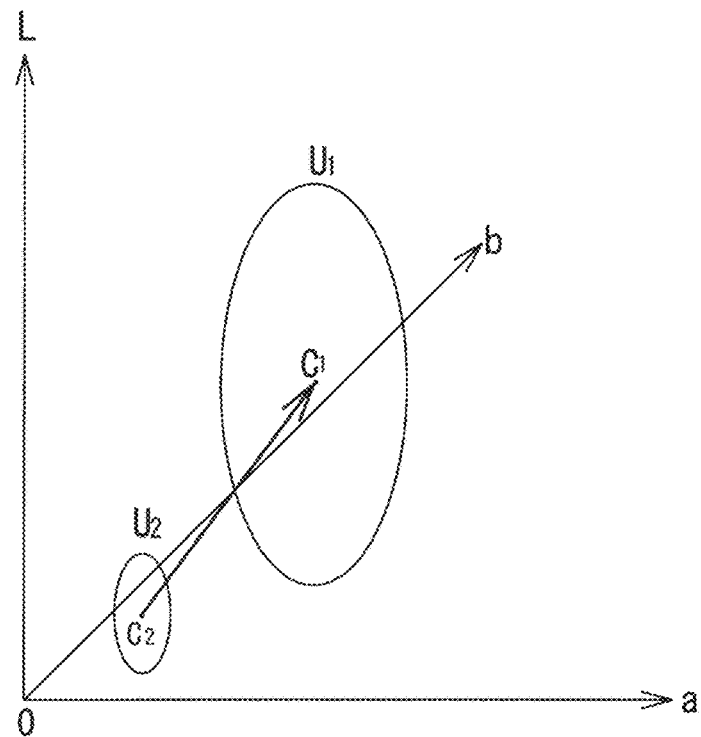
FIGS. 15A and 15B are diagrams illustrating a shift process in a Lab coordinate space performed by the texture evaluation apparatus 201 of metal surface according to Embodiment 3 of the present disclosure.
Figure 15B:
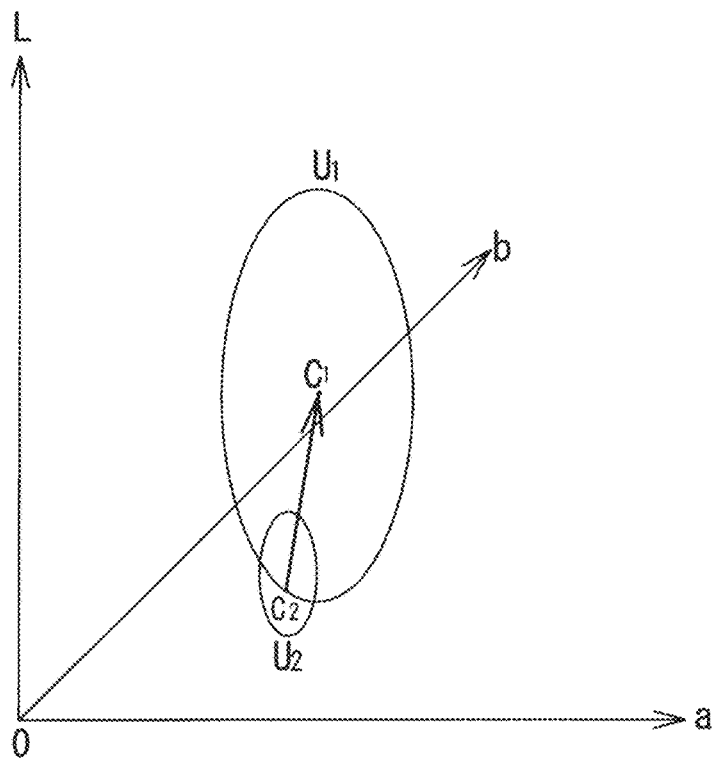

In computation of a chromaticity histogram distribution in the Lab space corresponding to the inspection area K, the XYZ values are converted into Lab values. The index is computed, based on distributions in a three-dimensional space of L, a and b axes. The Lab chromaticity distribution has a three-dimensional elliptical shape. As shown in FIGS. 15A and 15B, $U_1(L,a,b)$ and $U_2(L,a,b)$ respectively denote Lab values of the inspection plane and the reference plane in Lab space coordinates. In the Lab color space, each histogram distribution has a globe-like shape. Two histogram distributions may be three-dimensionally overlapped or may be three-dimensionally separated from each other. The inspection area K in the three-dimensional space is divided into grids. Three-dimensional chromaticity histogram distributions of $U_1(L,a,b)$ and $U_2(L,a,b)$ and minimum distribution are determined, and the index is computed similarly. An integrated number of grids may be projected on a plane, and an integrated number in an overlap area in the plane on the grids by similar integration. The Lab chromaticity includes brightness information, so that a change in brightness of the image leads to a change in L value in the Lab space. The distributions $U_1$ and $U_2$ of the degree of consistency are shifted in position in the Lab space. This allows for determination taking into account the brightness. This is because the different brightness of an image leads to the different position of the distribution. For example, the Lab color space histogram distribution is shifted downward with a decrease in brightness and is shifted upward with an increase in brightness.

The following describes other examples of applications. Two taken images, i.e., images A and B, of a reference plane and an inspection plane may be overlapped with each other, and their chromaticity histogram distributions may be displayed on the display unit 7. These chromaticity histogram distributions may be shown in an overlapping manner on one chromaticity diagram. The color difference may be determined by using average Lab values, while the texture spread index indicating the texture of the metal surface may be separately computed in percentage. This enables a deviation of the spatial spread of the chromaticity distribution of the inspection plane relative to the chromaticity distribution of the reference plane or more specifically the irregularity and the roughness to be checked numerically. The result of inspection is shown numerically with respect to each area K. The width of the grid is adjustable. The threshold value of the index may be set arbitrarily. The measurement results and the taken images may be stored. The aspects of the disclosure reduce the potential problem of individual difference which is inevitable in visual inspection and the potential trouble due to the difference from the clients' criterion of judgment and allows for standardization of the metal texture finishing and stable texture management.

The embodiments described above have the following advantageous effects. The embodiments show examples of (1) the average L value, the average a value and the average b value and (2) the texture spread index of the two distributions $H_1(x,y)$ and $H_2(x,y)$, the two distributions $T_1(X,Y,Z)$ and $T_2(X,Y,Z)$ and the two distributions $U_1(L,a,b)$ and $U_2(L,a,b)$. The difference in texture such as gloss, glaze, irregularity and the like is provided separately from the color. This ensures accurate and quick evaluation. The appropriate direction is given for the finishing quality by adjustment of the texture, such as adjustment of the roughness of the metal surface.

As shown in Examples 1 to 7, the roughness of the metal surface was measured for evaluation with the evaluation apparatus 1 of the metal surface according to the present disclosure.

The following describes the present disclosure more concretely with reference to some examples, although the present disclosure is not at all limited to these examples. The characteristic values of the respective examples were measured and evaluated as described below.

(1) Evaluation Apparatus

An evaluation apparatus PPLB-200 manufactured by PaPaLab Co., Ltd. was used. The apparatus PPLB-200 includes a two-dimensional colorimeter RC-500. A light D50 manufactured by Panasonic Corporation was used for lighting.

(2) Imaging

Imaging with the apparatus PPLB-200 was performed in a dark room. A still image-type two-dimensional colorimeter was used, and the measurement was performed on the assumption that the L value of a white plate was 100.

(3) Measurement Range

Figure 16:
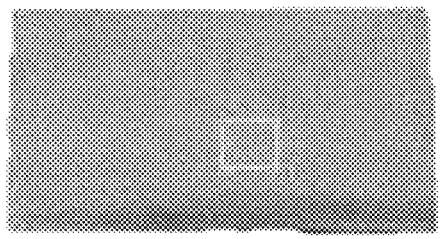
FIG. 16 is photographs illustrating measurement ranges and measurement locations (within the square frames of images) of sample No. 2 of Example 1.
Figure 16:
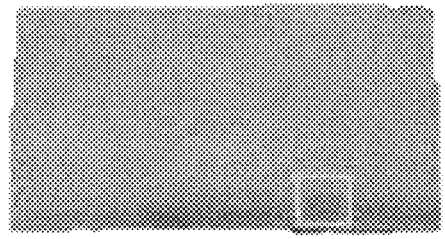
Figure 16:
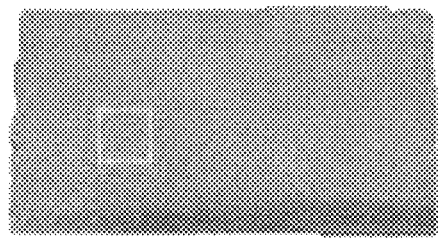
Figure 17:
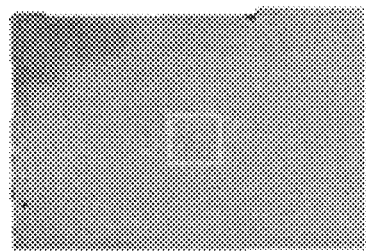
FIG. 17 is photographs illustrating measurement ranges and measurement locations (within the square frames of images) of sample No. 2 of Example 2.
Figure 17:
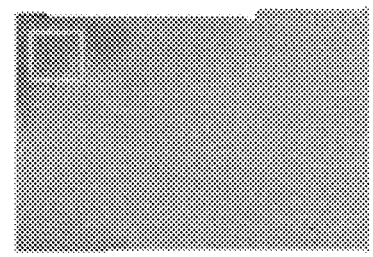
Figure 17:
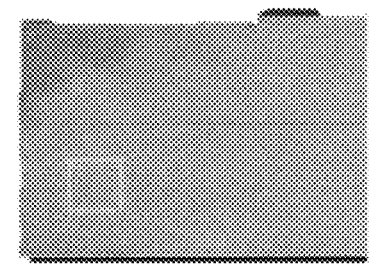
Figure 18:
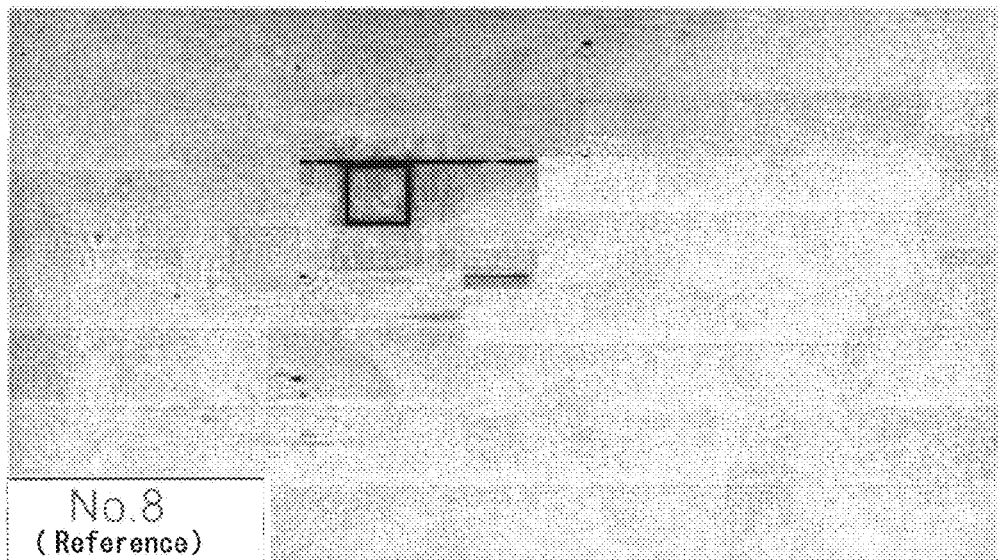
FIG. 18 is photographs illustrating measurement ranges and measurement locations (within the square frames of images) of samples No. 8 and No. 4 of Example 3.
Figure 18:
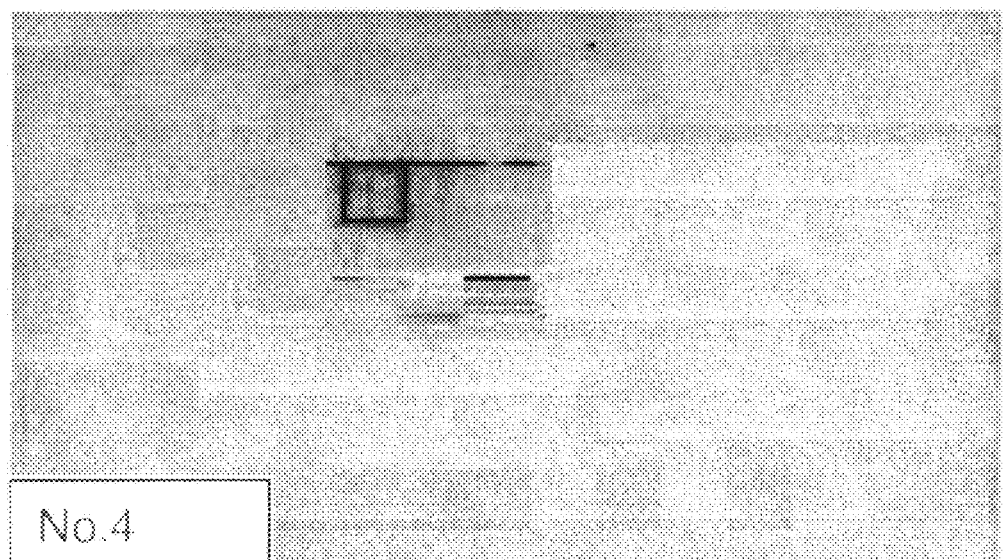
Figure 19:
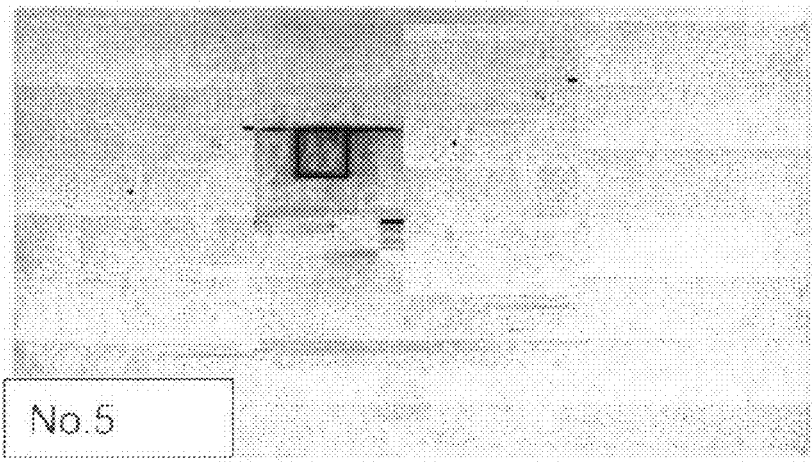
FIG. 19 is photographs illustrating measurement ranges and measurement locations (within the square frames of images) of samples No. 5 to No. 7 of Example 3.
Figure 19:
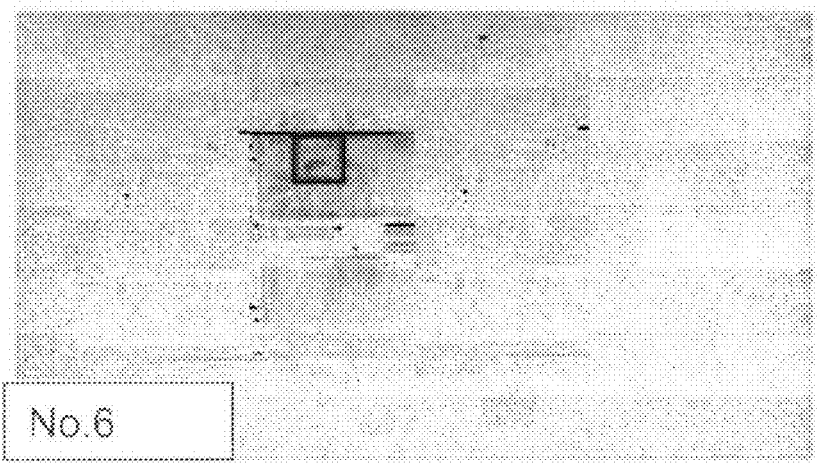
Figure 19:
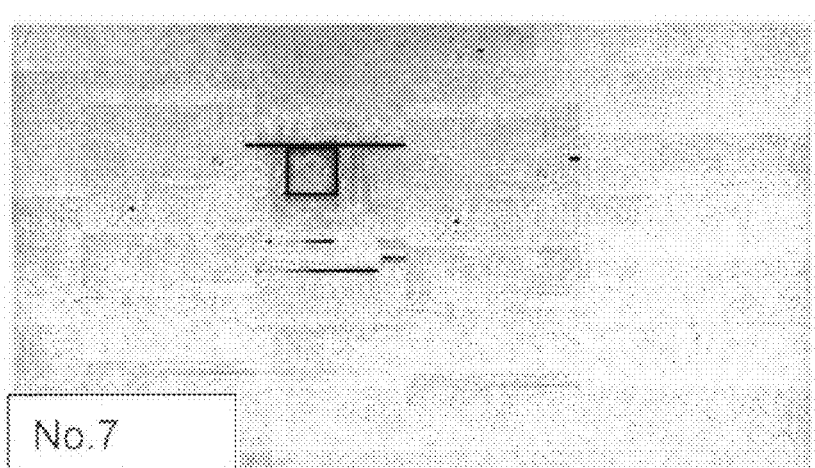

The measurement range for evaluation had an identical size in all the samples. The measurement ranges are shown by the square frame borders of respective images in FIG. 16 with respect to Example 1, in FIG. 17 with respect to Example 2 and in FIGS. 18 and 19 with respect to Example 3.

(4) Measurement Items and Results

An acceptable reference plane of a sample and inspection samples were measured. The degree of consistency, ΔE and differences of average Lab values were determined with respect to the taken reference and inspection sample images. With regard to the degree of consistency, the xy-3D value is a value determined without the shift process of the central coordinate of the histogram distribution (S147 in FIG. 6, S207 in FIG. 11 or S207 in FIG. 12), and the color separation value is a value determined with the shift process of the central coordinate of the histogram distribution. The color separation value is a parameter of separating the texture from the color. The differences of average Lab values are calculated by (average Lab values of inspection sample)−(average Lab values of reference sample). A sample having the most similar color and surface texture to those of the reference sample was identified, based on the measurement results of the degree of consistency and ΔE. The value ΔE used was ΔE00 taking into account the human visibility characteristic.

The following describes measurement locations, degrees of consistency, ΔE00, differences of average Lab values in a measurement range with respect to metal parts of Examples 1 to 3.

A non-brown turbidity portion of a metal surface of a sample No. 2 was specified as a reference, and the degree of consistency, ΔE00, and differences of average Lab values were measured with respect a brown turbidity portion and a non-brown turbidity portion (location different from the reference) of the sample No. 2. Table 2 shows a list of measurement results. Evaluation of the difference in texture with exclusion of the difference in color is based on color separation values. Evaluation of the difference in texture with the difference in color takes account of ΔE00 and the differences of average Lab values, in addition to the color separation values.

TABLE 2

Sample No.2

| Measurement portion | Degree of consistency | | Color separation | Difference of average Lab | | | |
|---|---|---|---|---|---|---|---|
| | xy-3D | | | ΔE00 | ΔL | Δa | Δb |
| Brown turbidity | 46% | | 63% | 3.530 | −3.866 | 0.717 | 2.454 |
| Non-brown turbidity | 96% | | 96% | 0.376 | −0.124 | 0.253 | −0.083 |

Lab values in a reference measurement range, Lab values in a measurement range of a brown turbidity portion and Lab values in a measurement range of a non-brown turbidity portion with respect to the sample No. 2 are respectively shown in Table 3, Table 4 and Table 5. With respect to the degree of consistency of the non-brown turbidity portion, both the xy-3D value and the color separation value are 96%. With respect to the degree of consistency of the brown turbidity portion, however, the color separation value is 63%, which is significantly higher than the xy-3D value of 46% by 17%. These results indicate the more accurate evaluation. This is accordingly closer to the human visual recognition of brown turbidity and thereby allows for quick and accurate evaluation.

TABLE 3

Sample No. 2 Reference
Lab value in measurement range

| L | a | b |
|---|---|---|
| 73.424 | 1.622 | 6.321 |

TABLE 4

Sample No. 2 Brown turbidity
Lab value in measurement range

| L | a | b |
|---|---|---|
| 71.733 | 1.848 | 7.424 |

TABLE 5

Sample No. 2 Non-brown turbidity
Lab value in measurement range

| L | a | b |
|---|---|---|
| 73.674 | 1.505 | 6.385 |

Example 2

A non-brown turbidity portion of a metal surface of a sample No. 3 was specified as a reference, and the degree of consistency, ΔE00, and differences of average Lab values were measured with respect a brown turbidity portion and a non-brown turbidity portion (location different from the reference) of the sample No. 3. Table 6 shows a list of measurement results. Evaluation of the difference in texture with exclusion of the difference in color is based on color separation values. Evaluation of the difference in texture with the difference in color takes account of ΔE00 and the differences of average Lab values, in addition to the color separation values.

TABLE 6

Sample No.3

| Measurement portion | Degree of consistency | | Difference of average Lab | | | |
|---|---|---|---|---|---|---|
| | xy-3D | Color separation | ΔE00 | ΔL | Δa | Δb |
| Brown turbidity | 66% | 80% | 5.217 | −6.696 | 0.433 | 0.691 |
| Non-brown turbidity | 96% | 96% | 0.345 | −0.350 | −0.168 | −0.078 |

Lab values in a reference measurement range, Lab values in a measurement range of a brown turbidity portion and Lab values in a measurement range of a non-brown turbidity portion with respect to the sample No. 3 are respectively shown in Table 7, Table 8 and Table 9. With respect to the degree of consistency of the non-brown turbidity portion, both the xy-3D value and the color separation value are 96%. With respect to the degree of consistency of the brown turbidity portion, however, the color separation value is 80%, which is significantly higher than the xy-3D value of 66% by 14%. These results indicate the more accurate evaluation. This is accordingly closer to the human visual recognition of brown turbidity and thereby allows for quick and accurate evaluation.

TABLE 7

Sample No. 3 Reference
Lab value in measurement range

| L | a | b |
|---|---|---|
| 73.553 | 2.105 | 6.281 |

TABLE 8

Sample No. 3 Brown turbidity
Lab value in measurement range

| L | a | b |
|---|---|---|
| 66.857 | 2.537 | 6.972 |

TABLE 9

Sample No. 3 Non-brown turbidity
Lab value in measurement range

| L | a | b |
|---|---|---|
| 73.203 | 1.937 | 6.203 |

Example 3

Samples No. 4 to No. 6 had white turbidity, and a sample No. 7 did not have white turbidity. A sample No. 8 without white turbidity was used as a reference. The degree of consistency, ΔE00, and differences of average Lab values were measured with respect to white turbidity portions of the samples No. 4 to No. 6. The sample No. 7 without white turbidity was similarly measured for the purpose of comparison. Table 10 shows a list of measurement results. Evaluation of the difference in texture with exclusion of the difference in color is based on color separation values. Evaluation of the difference in texture with the difference in color takes account of ΔE00 and the differences of average Lab values, in addition to the color separation values.

TABLE 10

Measurement result of sample with white turbidity by using sample No.8 as reference

| Sample No. | Degree of consistency | | Difference of average Lab | | | |
|---|---|---|---|---|---|---|
| | xy-3D | Color separation | ΔE00 | ΔL | Δa | Δb |
| No.4 | 59% | 61% | 14.190 | 16.946 | 3.703 | −1.987 |
| No.5 | 54% | 56% | 19.464 | 22.925 | 4.258 | −2.867 |
| No.6 | 67% | 67% | 11.437 | 13.739 | 3.221 | −1.592 |
| No.7 | 85% | 79% | 2.575 | 3.301 | 0.692 | −0.461 |

Lab values in a reference measurement range, Lab values in a measurement range of a white turbidity portion and Lab values in a measurement range of a non-white turbidity portion with respect to the samples No. 8 (reference), No. 4, No. 5, No. 6 and No. 7 are respectively shown in Table 11, Table 12, Table 13, Table 14 and Table 15. With respect to the degree of consistency in the non-white turbidity portion of the sample, the color separation value is 79%, which is lower than the xy-3D value of 85%. With respect to the degree of consistency in the samples No. 4 to No. 6 with white turbidity, however, the color separation values are respectively 61%, 56% and 67%, which are all higher than the corresponding xy-3D values by 2%. These results indicate the more accurate evaluation. This is accordingly closer to the human visual recognition of white turbidity and thereby allows for quick and accurate evaluation.

TABLE 11

No. 8 (Reference)
Lab value in measurement range

| L | a | b |
|---|---|---|
| 21.812 | −1.804 | −5.339 |

TABLE 12

No. 4 (Sample with white turbidity)
Lab value in measurement range

| L | a | b |
|---|---|---|
| 38.758 | 1.899 | −7.326 |

TABLE 13

No. 5 (Sample with white turbidity)
Lab value in measurement range

| L | a | b |
|---|---|---|
| 44.737 | 2.454 | −8.206 |

TABLE 14

No. 6 (Sample with white turbidity)
Lab value in measurement range

| L | a | b |
|---|---|---|
| 35.551 | 1.417 | −6.931 |

TABLE 15

No. 7 (Sample with white turbidity)
Lab value in measurement range

| L | a | b |
|---|---|---|
| 25.113 | −1.112 | −5.800 |

The present disclosure is not limited to the above embodiments, but various modifications may be made to the embodiments without departing from the scope of the disclosure. Such modifications as well as their equivalents are also included in the scope of the disclosure. The disclosure may be implemented by various aspects within the scope of the disclosure. The methods of obtaining image information according to three spectral sensitivities (S1(λ), S2(λ), S3(λ)) described in the above embodiments are only illustrative and are not restrictive. The technical feature of the disclosure may also be achieved by any other suitable method.

INDUSTRIAL APPLICABILITY

The evaluation apparatus of the present disclosure is configured to quantify the texture such as gloss, glaze, irregularity and the like of the metal surface by diffraction phenomenon of illumination light. This quantification is significantly close to the human visual recognition. The evaluation apparatus of the disclosure is thus applicable to evaluation of the irregularity of the metal surface or the like, which conventionally depends on the human visual recognition.

REFERENCE SIGNS LIST 1, 101, 201 . . . texture evaluation apparatus of metal surface
2, 102, 202 . . . two-dimensional colorimeter
3, 103, 203 . . . arithmetic processor
5, 105, 205 . . . metal surface
6, 106, 206 . . . lighting unit
7 . . . display device
21 . . . photographic lens
22a, 22b, 22c . . . optical filters
23 . . . imaging element
22a', 22c' . . . dichroic mirrors
23a, 23b, 23c . . . imaging elements

The invention claimed is:

1. A texture evaluation apparatus of a metal surface, comprising:
   a camera configured to have three spectral sensitivities (S1(λ), S2(λ), S3(λ)) linearly and equivalently converted to a CIE XYZ color matching function;
   an arithmetic processor configured to obtain and compute data by conversion of an image that has three spectral sensitivities and that is obtained by the camera into tristimulus values X, Y and Z in a CIE XYZ color system; and
   a light source configured to illuminate a metal surface, wherein
   the arithmetic processor is configured to:
   set a specified inspection area out of data obtained by imaging the metal surface;
   divide the inspection area into grids in coordinates corresponding to a color space in an XYZ color system, and integrate number of pixels included in each grid with respect to an inspection plane and a reference plane, so as to create respective color space histogram distributions in the XYZ color system; and
   identify centers of the two color space histogram distributions of the inspection plane and the reference plane, and compute a texture spread index indicating a difference in spread between the color space histogram distributions by shifting the center of one of the color space histogram distributions to be closer to the other color space histogram distribution.

2. A texture evaluation method of a metal surface using a camera configured to have three spectral sensitivities (S1(λ), S2(λ), S3(λ)) linearly and equivalently converted to a CIE XYZ color matching function, the texture evaluation method comprising:
   generating data by conversion of an image that has three spectral sensitivities and that is obtained by imaging with the camera under lighting into tristimulus values X, Y and Z in a CIE XYZ color system;
   setting a specified inspection area out of data obtained by imaging a metal surface;
   dividing the inspection area into grids in coordinates corresponding to a color space in an XYZ color system, and integrating number of pixels included in each grid with respect to an inspection plane and a reference plane, so as to create respective color space histogram distributions in the XYZ color system; and
   identifying centers of the two color space histogram distributions of the inspection plane and the reference plane, and computing a texture spread index indicating a difference in spread between the color space histogram distributions by shifting the center of one of the color space histogram distributions to be closer to the other color space histogram distribution.

* * * * *